US011459586B2

(12) United States Patent
Church et al.

(10) Patent No.: US 11,459,586 B2
(45) Date of Patent: Oct. 4, 2022

(54) METHODS FOR INCREASING EFFICIENCY OF NUCLEASE-MEDIATED GENE EDITING IN STEM CELLS

(71) Applicant: President and Fellows of Harvard College, Cambridge, MA (US)

(72) Inventors: George M. Church, Brookline, MA (US); Susan M. Byrne, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 507 days.

(21) Appl. No.: 16/094,011

(22) PCT Filed: Apr. 19, 2017

(86) PCT No.: PCT/US2017/028266
§ 371 (c)(1),
(2) Date: Oct. 16, 2018

(87) PCT Pub. No.: WO2017/184674
PCT Pub. Date: Oct. 26, 2017

(65) Prior Publication Data
US 2019/0127762 A1 May 2, 2019

Related U.S. Application Data

(60) Provisional application No. 62/324,485, filed on Apr. 19, 2016.

(51) Int. Cl.
*C12N 15/00* (2006.01)
*C12N 15/90* (2006.01)
*C12N 9/22* (2006.01)
*C12N 5/0735* (2010.01)
*C12N 5/0793* (2010.01)
*C12N 5/0775* (2010.01)
*C12N 5/074* (2010.01)

(52) U.S. Cl.
CPC ......... *C12N 15/907* (2013.01); *C12N 5/0606* (2013.01); *C12N 5/0619* (2013.01); *C12N 5/0663* (2013.01); *C12N 9/22* (2013.01); *C12N 5/0696* (2013.01); *C12N 2310/20* (2017.05); *C12N 2740/16043* (2013.01)

(58) Field of Classification Search
CPC .. C12N 15/907; C12N 5/0606; C12N 5/0619; C12N 5/0663; C12N 9/22; C12N 2310/20; C12N 5/0696; C12N 2740/16043
See application file for complete search history.

(56) References Cited

U.S. PATENT DOCUMENTS

2016/0333377 A1* 11/2016 Scharenberg ........... A61P 35/00

OTHER PUBLICATIONS

Zhang, et al. CRISPR/Cas9-Mediated Genome Editing in Human Pluripotent Stem Cells. IN: Springer Briefs in Stem Cells, vol. 6: Hematopoietic Differentiation of Human Pluripotent. Stem Cells 2015, p. 103-116). (Year: 2015).*
Kawamura, et al. Linking the p53 tumor suppressor pathway to somatic cell reprogramming. Nature 2009, 460(7259): pp. 1140-1144). (Year: 2009).*
Kawamura et al (Nature 2009, vol. 460 (7259) pp. 1140-1144 (IDS reference). (Year: 2009).*
Cheng et al (JBC vol. 276, No. 46, Nov. 16, 2001: pp. 43320-43327). (Year: 2001).*
Cheng et al (JBC vol. 276, No. 46, Nov. 16, 2001: pp. 43320-43327; clearer copy). (Year: 2001).*
Chang et al (Cell Reports 2015, vol. 12: pp. 1668-1677). (Year: 2015).*
Kawamura, et al. Linking the p53 tumor suppressor pathway to somatic cell reprogramming. Nature 2009, 460 (7259):1140-1144; Abstract, p. 3 [according to the posted document].
Zhang, et al. CRISPR/Cas9-Mediated Genome Editing in Human Pluripotent Stem Cells. IN: Springer Briefs in Stem Cells, vol. 6: Hematopoietic Differentiation of Human Pluripotent Stem Cells 2015, p. 103-116; Abstract, p. 105, 107, 108, 110, 111, 114, 115.

* cited by examiner

*Primary Examiner* — Catherine S Hibbert
(74) *Attorney, Agent, or Firm* — Banner & Witcoff, Ltd.

(57) ABSTRACT

Inhibiting p53 or Bax can be used to improve nuclease-mediated gene targeting frequencies in stem cells. This inhibition can be achieved, e.g., by overexpression of anti-apoptosis proteins or by silencing or reducing p53 or Bax expression. This technique can be used in conjunction with other rapidly developing CRISPR technologies, including improvements in specificity, other types of nucleases, and further enrichment, screening, and selection schemes, to expand the use of stem cells in experimental studies and tissue engineering for therapeutic purposes.

12 Claims, 31 Drawing Sheets
Specification includes a Sequence Listing.

Transfect with plasmids encoding:
- mThy1 donor
- Cas9 nuclease expressed with anti-apoptotic gene
- Left, Right, Both, or No Thy1 sgRNAs Human iPSC → 5 days → FACS analysis for mThy1 and hThy1 on iPSC

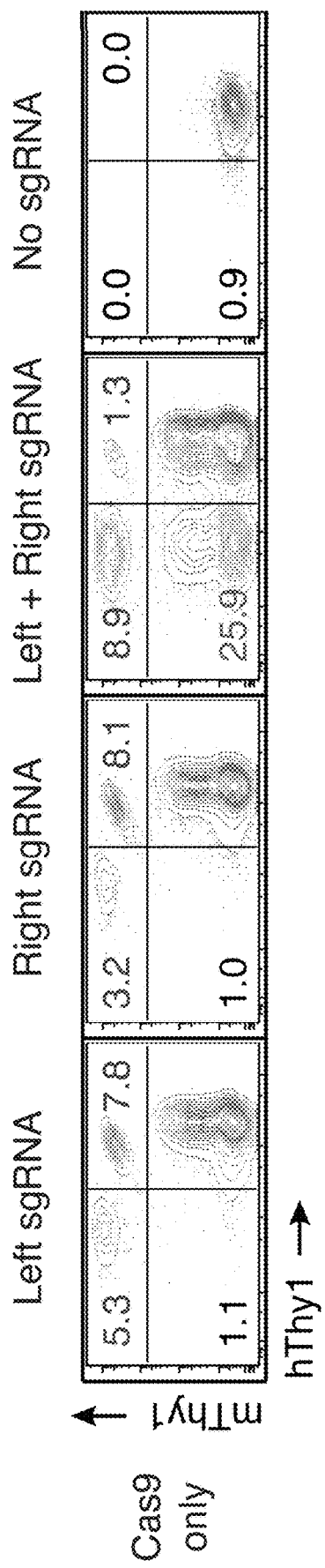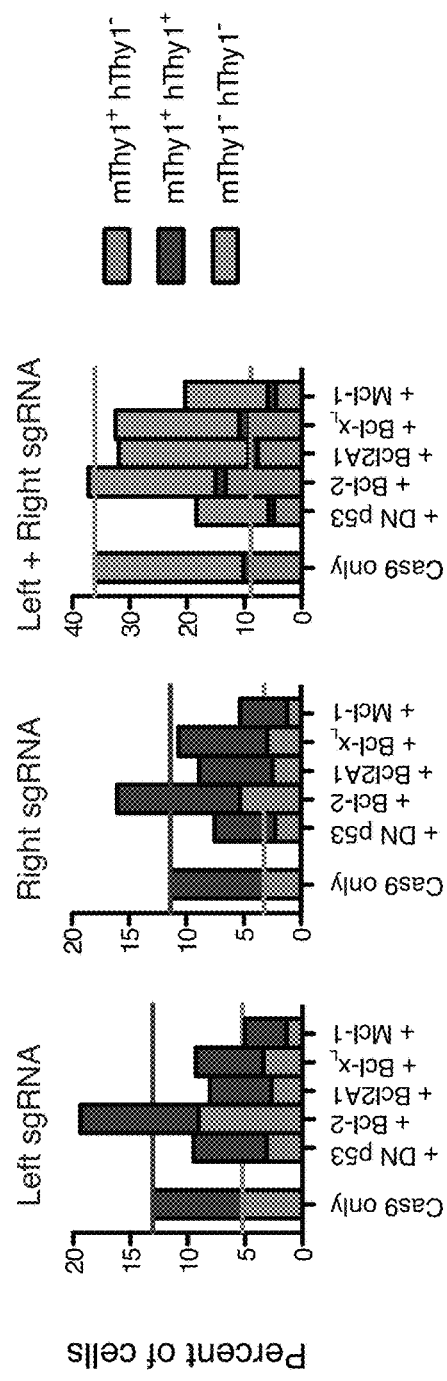
FIG. 4C
FIG. 4D

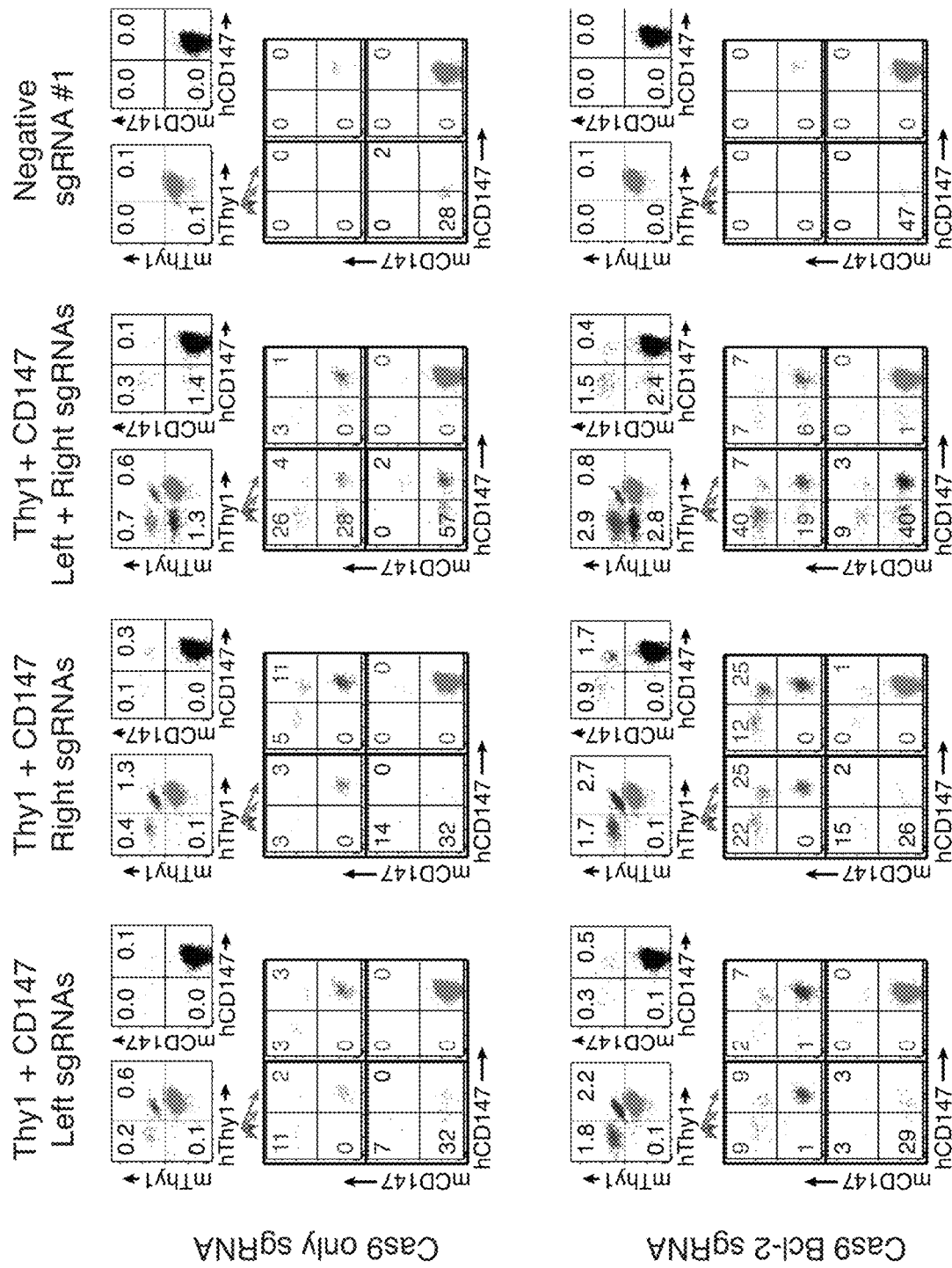
FIGG. 5B

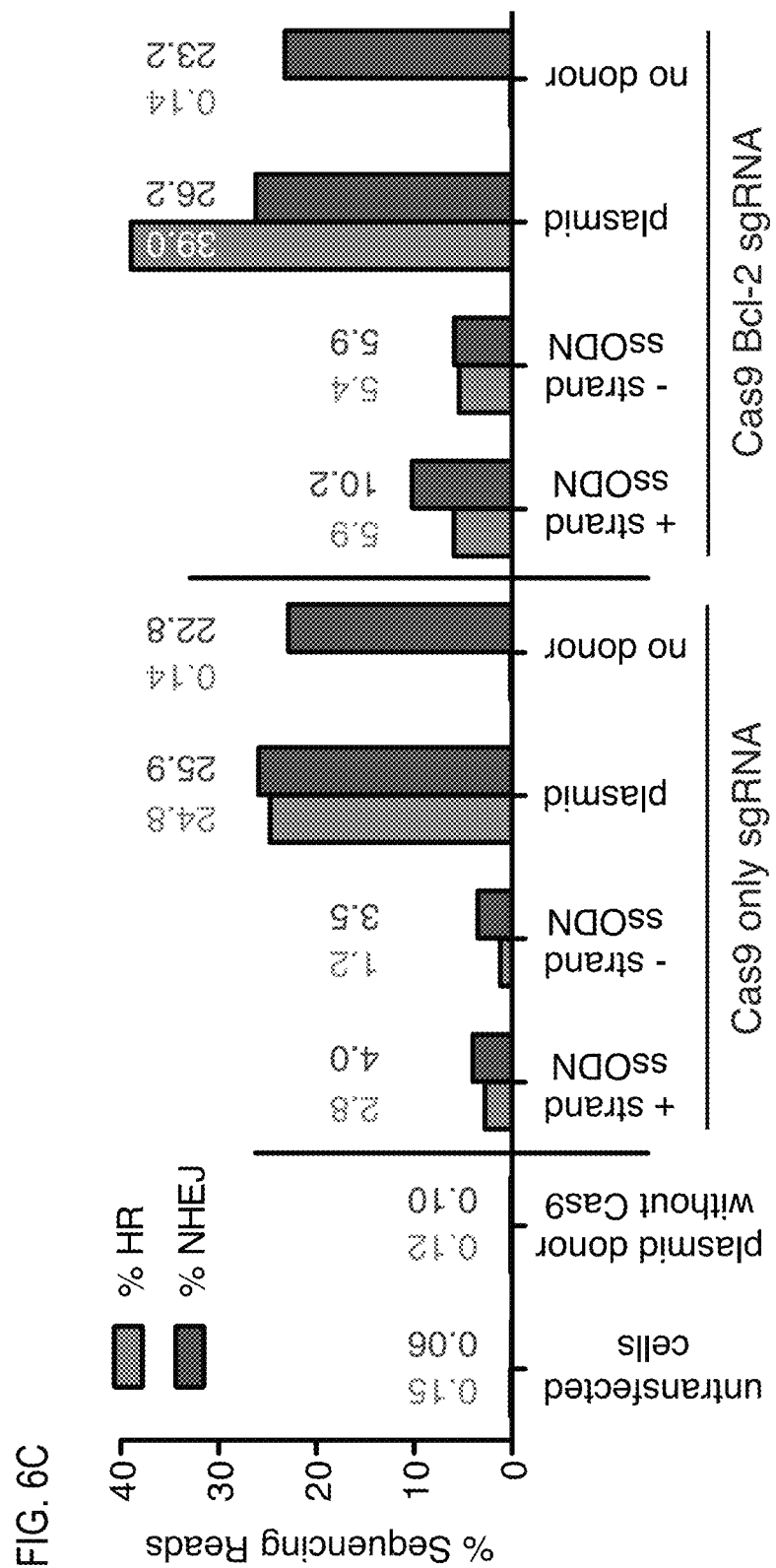

Transfect with plasmids encoding:
- mThy1 or mCD147 donor
- Cas9 nuclease expressed with IRES Bcl-2 along with an sgRNA Transfect with plasmids encoding:
- mThy1 donor
- Cas9 nuclease
- Left, Right, Both, or No Thy1 sgRNAs

| # of colonies after single cell FACS sort (out of 190) | SMC4 | SMC4 + zVAD | Increase |
|---|---|---|---|
| PGP1 iPSC (retroviral) | 94 | 109 | 116% |
| PGP1 iPSC (non-integrated) | 68 | 78 | 114% |

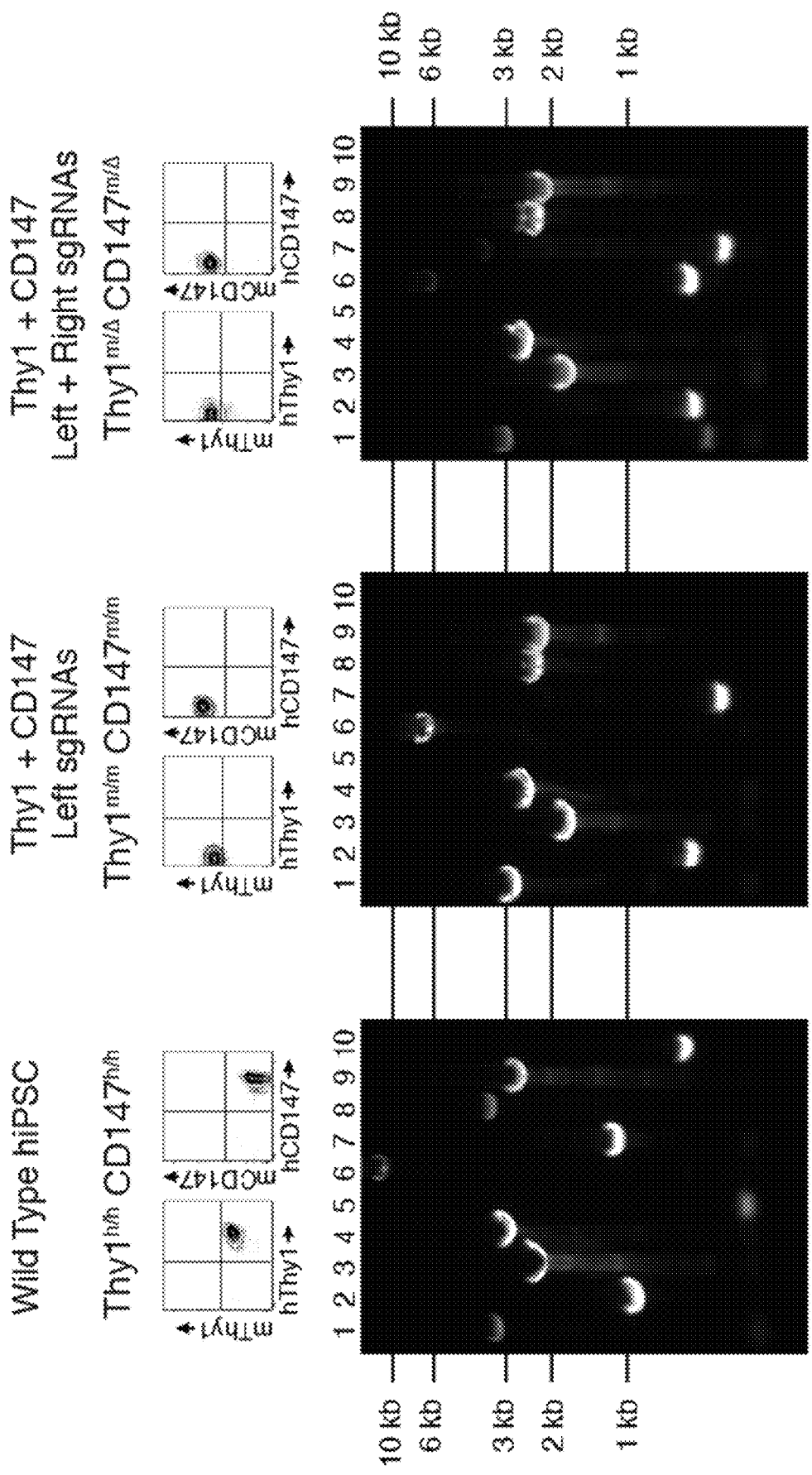
FIGG. 11B

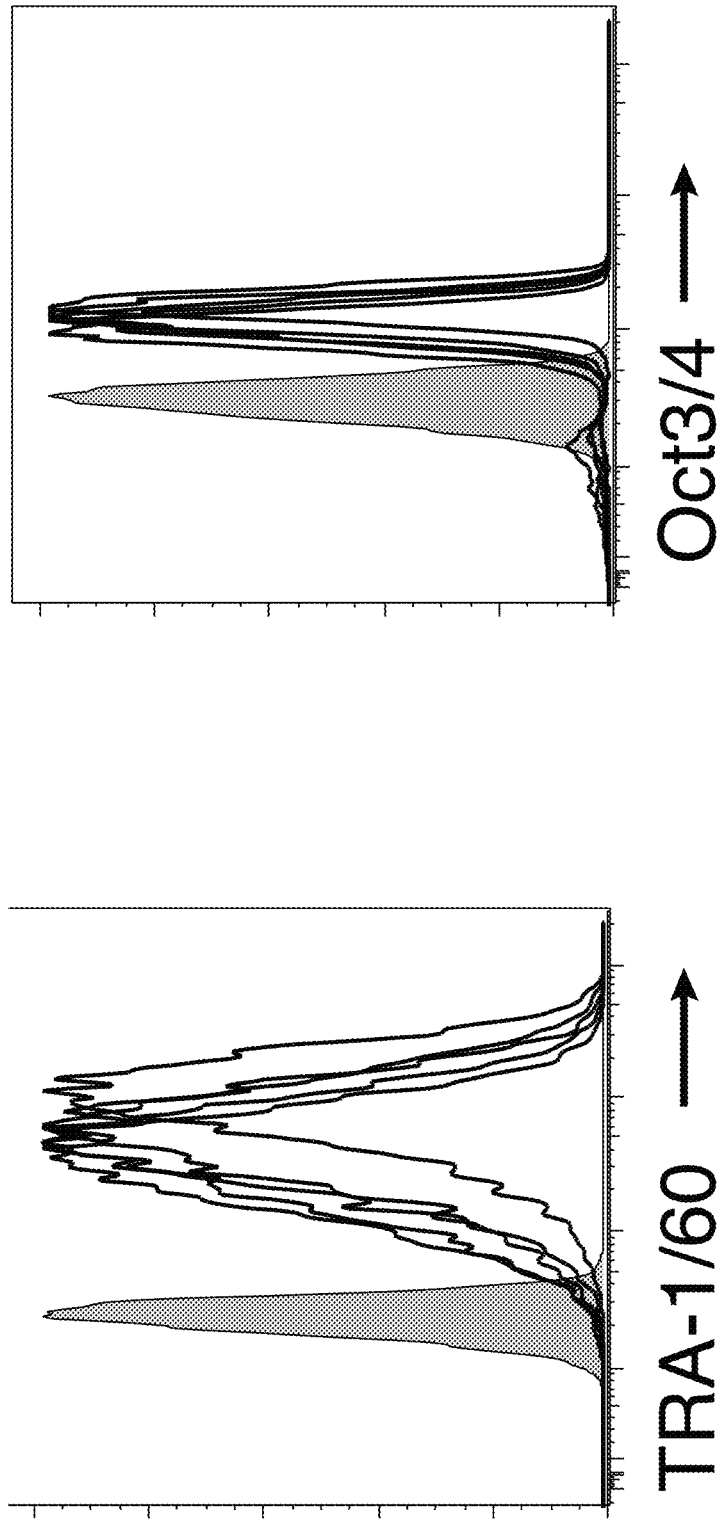

SEQUENCE LISTING

```
<160> NUMBER OF SEQ ID NOS: 43

<210> SEQ ID NO 1
<211> LENGTH: 23
<212> TYPE: DNA
<213> ORGANISM: Artificial
<220> FEATURE:
<223> OTHER INFORMATION: THY1 coding exon sgRNA

<400> SEQUENCE: 1
gggtcaggct gaactcgtac tgg                                              23

<210> SEQ ID NO 2
<211> LENGTH: 21
<212> TYPE: DNA
<213> ORGANISM: Artificial
<220> FEATURE:
<223> OTHER INFORMATION: THY1 truncated sgRNA

<400> SEQUENCE: 2
gtcaggctga actcgtactg g                                                21

<210> SEQ ID NO 3
<211> LENGTH: 23
<212> TYPE: DNA
<213> ORGANISM: Artificial
<220> FEATURE:
<223> OTHER INFORMATION: POU5F1 coding exon sgRNA

<400> SEQUENCE: 3
gctggagcaa aacccggagg agg                                              23

<210> SEQ ID NO 4
<211> LENGTH: 21
<212> TYPE: DNA
<213> ORGANISM: Artificial
<220> FEATURE:
<223> OTHER INFORMATION: negative sgRNA #1

<400> SEQUENCE: 4
gcttcaaaga acggcgctaa c                                                21

<210> SEQ ID NO 5
<211> LENGTH: 21
```

-continued

```
<212> TYPE: DNA
<213> ORGANISM: Artificial
<220> FEATURE:
<223> OTHER INFORMATION: negative sgRNA #2

<400> SEQUENCE: 5
ggagacgatt aatgcgtctc g                                          21

<210> SEQ ID NO 6
<211> LENGTH: 23
<212> TYPE: DNA
<213> ORGANISM: Artificial
<220> FEATURE:
<223> OTHER INFORMATION: CD147 coding exon sgRNA

<400> SEQUENCE: 6
gtcgtcagaa cacatcaacg agg                                        23

<210> SEQ ID NO 7
<211> LENGTH: 22
<212> TYPE: DNA
<213> ORGANISM: Artificial
<220> FEATURE:
<223> OTHER INFORMATION: CD147 truncated sgRNA

<400> SEQUENCE: 7
gcgtcagaac acatcaacga gg                                         22

<210> SEQ ID NO 8
<211> LENGTH: 23
<212> TYPE: DNA
<213> ORGANISM: Artificial
<220> FEATURE:
<223> OTHER INFORMATION: THY1 left sgRNA

<400> SEQUENCE: 8
gcacagtctc agaaaagcgc agg                                        23

<210> SEQ ID NO 9
<211> LENGTH: 23
<212> TYPE: DNA
<213> ORGANISM: Artificial
<220> FEATURE:
<223> OTHER INFORMATION: THY1 right sgRNA

<400> SEQUENCE: 9
gttagtagca acgctacccc agg                                        23

<210> SEQ ID NO 10
<211> LENGTH: 24
<212> TYPE: DNA
<213> ORGANISM: Artificial
<220> FEATURE:
<223> OTHER INFORMATION: CD147 left sgRNA

<400> SEQUENCE: 10
gatttcctgc gctgaatcgg gtgg                                       24

<210> SEQ ID NO 11
<211> LENGTH: 24
<212> TYPE: DNA
<213> ORGANISM: Artificial
<220> FEATURE:
<223> OTHER INFORMATION: CD147 right sgRNA

<400> SEQUENCE: 11
```

```
gtggctcctg tctgtgcctg acgg                                              24

<210> SEQ ID NO 12
<211> LENGTH: 24
<212> TYPE: DNA
<213> ORGANISM: Artificial
<220> FEATURE:
<223> OTHER INFORMATION: Jak2 sgRNA

<400> SEQUENCE: 12
gaattatgga gtatgtgtct gtgg                                              24

<210> SEQ ID NO 13
<211> LENGTH: 23
<212> TYPE: DNA
<213> ORGANISM: Artificial
<220> FEATURE:
<223> OTHER INFORMATION: HLA-A sgRNA

<400> SEQUENCE: 13
ggacctgcgc tcttggaccg cgg                                               23

<210> SEQ ID NO 14
<211> LENGTH: 22
<212> TYPE: DNA
<213> ORGANISM: Artificial
<220> FEATURE:
<223> OTHER INFORMATION: HLA-A trunctated sgRNA

<400> SEQUENCE: 14
gacctgcgct cttggaccgc gg                                                22

<210> SEQ ID NO 15
<211> LENGTH: 23
<212> TYPE: DNA
<213> ORGANISM: Artificial
<220> FEATURE:
<223> OTHER INFORMATION: HLA-B or C sgRNA

<400> SEQUENCE: 15
gggccgcctc ccacttgcgc tgg                                               23

<210> SEQ ID NO 16
<211> LENGTH: 21
<212> TYPE: DNA
<213> ORGANISM: Artificial
<220> FEATURE:
<223> OTHER INFORMATION: HLA-B or C truncated sgRNA

<400> SEQUENCE: 16
gccgcctccc acttgcgctg g                                                 21

<210> SEQ ID NO 17
<211> LENGTH: 28
<212> TYPE: DNA
<213> ORGANISM: Artificial
<220> FEATURE:
<223> OTHER INFORMATION: Y28A primer

<400> SEQUENCE: 17
gtcgcagagg ggcgccgagt gggatgcg                                          28

<210> SEQ ID NO 18
<211> LENGTH: 28
<212> TYPE: DNA
<213> ORGANISM: Artificial
```

```
<220> FEATURE:
<223> OTHER INFORMATION: Y28A primer

<400> SEQUENCE: 18
cgcatcccac tcggcgcccc tctgcgac                                              28

<210> SEQ ID NO 19
<211> LENGTH: 29
<212> TYPE: DNA
<213> ORGANISM: Artificial
<220> FEATURE:
<223> OTHER INFORMATION: G145A primer

<400> SEQUENCE: 19
aggccacaat cctcgcccag ttcaccccg                                             29

<210> SEQ ID NO 20
<211> LENGTH: 29
<212> TYPE: DNA
<213> ORGANISM: Artificial
<220> FEATURE:
<223> OTHER INFORMATION: G145A primer

<400> SEQUENCE: 20
cggggtgaac tgggcgagga ttgtggcct                                             29

<210> SEQ ID NO 21
<211> LENGTH: 109
<212> TYPE: DNA
<213> ORGANISM: Artificial
<220> FEATURE:
<223> OTHER INFORMATION: ssODN encoding Jak2 V617 mutation (plus)

<400> SEQUENCE: 21
aagtatgatg agcaagcttt ctcacaagca tttggtttta aattatggag tatgttctgt           60
ggagacgaga gtaagtaaaa ctacaggctt tctaatgcct ttctcagag                      109

<210> SEQ ID NO 22
<211> LENGTH: 110
<212> TYPE: DNA
<213> ORGANISM: Artificial
<220> FEATURE:
<223> OTHER INFORMATION: ssODN encoding Jak2 V617 mutation (minus)

<400> SEQUENCE: 22
ctctgagaaa ggcattagaa agcctgtagt tttacttact ctcgtctcca cagaaacata          60
ctccataatt taaaccaaa tgcttgtgag aaagcttgct catcatactt                      110

<210> SEQ ID NO 23
<211> LENGTH: 25
<212> TYPE: DNA
<213> ORGANISM: Artificial
<220> FEATURE:
<223> OTHER INFORMATION: primer

<400> SEQUENCE: 23
gtgcaggctt tcaacaatta ctttg                                                25

<210> SEQ ID NO 24
<211> LENGTH: 38
<212> TYPE: DNA
<213> ORGANISM: Artificial
<220> FEATURE:
<223> OTHER INFORMATION: primer
```

<400> SEQUENCE: 24
tctcgtctcc acagaaacat actccataat ttaaaacc                             38

<210> SEQ ID NO 25
<211> LENGTH: 46
<212> TYPE: DNA
<213> ORGANISM: Artificial
<220> FEATURE:
<223> OTHER INFORMATION: primer

<400> SEQUENCE: 25
attatggagt atgtttctgt ggagacgaga gtaagtaaaa ctacag                    46

<210> SEQ ID NO 26
<211> LENGTH: 24
<212> TYPE: DNA
<213> ORGANISM: Artificial
<220> FEATURE:
<223> OTHER INFORMATION: primer

<400> SEQUENCE: 26
atcttgctct agattgggct ttgg                                            24

<210> SEQ ID NO 27
<211> LENGTH: 52
<212> TYPE: DNA
<213> ORGANISM: Artificial
<220> FEATURE:
<223> OTHER INFORMATION: primer

<400> SEQUENCE: 27
cttgagccaa agcccaatct agagcaagat tagacgtcag gtggcacttt tc             52

<210> SEQ ID NO 28
<211> LENGTH: 52
<212> TYPE: DNA
<213> ORGANISM: Artificial
<220> FEATURE:
<223> OTHER INFORMATION: primer

<400> SEQUENCE: 28
ctttacaaag taattgttga aagcctgcac gtttgcgtat tgggcgctct tc             52

<210> SEQ ID NO 29
<211> LENGTH: 54
<212> TYPE: DNA
<213> ORGANISM: Artificial
<220> FEATURE:
<223> OTHER INFORMATION: primer

<400> SEQUENCE: 29
ctttccctac acgacgctct tccgatcttt atggacaaca gtcaaacaac aatt           54

<210> SEQ ID NO 30
<211> LENGTH: 53
<212> TYPE: DNA
<213> ORGANISM: Artificial
<220> FEATURE:
<223> OTHER INFORMATION: primer

<400> SEQUENCE: 30
ggagttcaga cgtgtgctct tccgatctac acctagctgt gatcctgaaa ctg            53

<210> SEQ ID NO 31
<211> LENGTH: 5

```
<212> TYPE: PRT
<213> ORGANISM: Artificial
<220> FEATURE:
<223> OTHER INFORMATION: peptide V5

<400> SEQUENCE: 31

Val Pro Met Leu Lys
1               5

<210> SEQ ID NO 32
<211> LENGTH: 5
<212> TYPE: PRT
<213> ORGANISM: Artificial
<220> FEATURE:
<223> OTHER INFORMATION: control peptide

<400> SEQUENCE: 32

Ile Pro Met Ile Lys
1               5

<210> SEQ ID NO 33
<211> LENGTH: 20
<212> TYPE: DNA
<213> ORGANISM: Artificial
<220> FEATURE:
<223> OTHER INFORMATION: sgRNA

<400> SEQUENCE: 33
aattatggag tatgtgtctg                                                      20

<210> SEQ ID NO 34
<211> LENGTH: 40
<212> TYPE: DNA
<213> ORGANISM: Artificial
<220> FEATURE:
<223> OTHER INFORMATION: ssODN

<400> SEQUENCE: 34
ttttaaatta tggagtatgt ttctgtggag acgagagtaa                                40

<210> SEQ ID NO 35
<211> LENGTH: 40
<212> TYPE: DNA
<213> ORGANISM: Artificial
<220> FEATURE:
<223> OTHER INFORMATION: ssODN

<400> SEQUENCE: 35
ttactctcgt ctccacagaa acatactcca taatttaaaa                                40

<210> SEQ ID NO 36
<211> LENGTH: 20
<212> TYPE: DNA
<213> ORGANISM: Artificial
<220> FEATURE:
<223> OTHER INFORMATION: sgRNA

<400> SEQUENCE: 36
gggtcaggct gaactcgtac                                                      20

<210> SEQ ID NO 37
<211> LENGTH: 18
<212> TYPE: DNA
<213> ORGANISM: Artificial
<220> FEATURE:
<223> OTHER INFORMATION: sgRNA
```

```
<400> SEQUENCE: 37
gtcaggctga actcgtac                                          18

<210> SEQ ID NO 38
<211> LENGTH: 20
<212> TYPE: DNA
<213> ORGANISM: Artificial
<220> FEATURE:
<223> OTHER INFORMATION: sgRNA

<400> SEQUENCE: 38
gtcgtcagaa cacatcaacg                                        20

<210> SEQ ID NO 39
<211> LENGTH: 19
<212> TYPE: DNA
<213> ORGANISM: Artificial
<220> FEATURE:
<223> OTHER INFORMATION: sgRNA

<400> SEQUENCE: 39
gcgtcagaac acatcaacg                                         19

<210> SEQ ID NO 40
<211> LENGTH: 20
<212> TYPE: DNA
<213> ORGANISM: Artificial
<220> FEATURE:
<223> OTHER INFORMATION: sgRNA

<400> SEQUENCE: 40
ggacctgcgc tcttggaccg                                        20

<210> SEQ ID NO 41
<211> LENGTH: 19
<212> TYPE: DNA
<213> ORGANISM: Artificial
<220> FEATURE:
<223> OTHER INFORMATION: sgRNA

<400> SEQUENCE: 41
gacctgcgct cttggaccg                                         19

<210> SEQ ID NO 42
<211> LENGTH: 20
<212> TYPE: DNA
<213> ORGANISM: Artificial
<220> FEATURE:
<223> OTHER INFORMATION: sgRNA

<400> SEQUENCE: 42
gggccgcctc ccacttgcgc                                        20

<210> SEQ ID NO 43
<211> LENGTH: 18
<212> TYPE: DNA
<213> ORGANISM: Artificial
<220> FEATURE:
<223> OTHER INFORMATION: sgRNA

<400> SEQUENCE: 43
gccgcctccc acttgcgc                                          18
```

METHODS FOR INCREASING EFFICIENCY OF NUCLEASE-MEDIATED GENE EDITING IN STEM CELLS

RELATED APPLICATION DATA

This application is a National Stage Application under 35 U.S.C. 371 of co-pending PCT application PCT/US17/28266 designating the United States and filed Apr. 19, 2017; which claims the benefit of U.S. provisional application No. 62/324,485 and filed Apr. 19, 2016 each of which are hereby incorporated by reference in their entireties.

STATEMENT OF GOVERNMENT INTERESTS

This invention was made with government support under HG005550 and HG008525 awarded by the National Institutes of Health and 0540879 awarded by the National Science Foundation. The government has certain rights in the invention.

Each reference cited in this disclosure is incorporated herein by reference in its entirety.

This application incorporates by reference the contents of a 6,129 bytes text file created on Apr. 11, 2016 and named "PCT_Sequence_Listing.txt," which is the sequence listing for this application.

TECHNICAL FIELD

This disclosure relates generally to gene editing.

BACKGROUND

The CRISPR type II system has been used to edit the genomes of a broad spectrum of species (see, e.g., Friedland et al., 2013; Mali et al., 2013; Hwang et al., 2013; Jiang et al., 2013; Jinek et al., 2013; Cong et al., 2013; Yin et al., 2014). CRISPR is particularly customizable because the active form consists of an invariant Cas9 protein and an easily programmable single guide RNA (sgRNA). Jinek et al., 2012. Of the various CRISPR orthologs, the *Streptococcus pyogenes* (Sp) CRISPR is the most well-characterized and widely used. The Cas9-gRNA complex first probes DNA for the protospacer-adjacent motif (PAM) sequence (–NGG for Sp Cas9), after which Watson-Crick base-pairing between the sgRNA and target DNA proceeds in a ratchet mechanism to form an R-loop. Following formation of a ternary complex of Cas9, sgRNA, and target DNA, the Cas9 protein generates two nicks in the target DNA, creating a blunt double-strand break (DSB) that is repaired by the non-homologous end joining (NHEJ) pathway or template-directed homologous recombination (HR). CRISPR methods are disclosed, for example, in U.S. Pat. Nos. 9,023,649 and 8,697,359.

The development of CRISPR/Cas9 nucleases has enormously expanded our ability to engineer genetic changes in human cells (Mali et al., 2013). But while immortalized human tumor cell lines have been edited with almost complete efficiency (Fu et al., 2014), gene editing in human stem cells has proved more challenging. Tumor cell lines are favored for their robustness, but they also possess unchecked proliferation, gross mutations, and abnormal responses to DNA damage. Genome engineering in human induced pluripotent stem cells (hiPSC) is therefore desired for developing scientific disease models or potential gene therapies. Their self-renewing capability allows hiPSC to be gene targeted, cloned, genotyped, and expanded, unlike primary tissues with limited growth potential. Edited pluripotent clones can then be differentiated into a variety of other cell types to analyze the phenotypic effect of the engineered mutations or employ reporter constructs.

Unfortunately, much lower gene editing rates have been achieved in human iPSC compared to tumor cell lines (Mali et al., 2013). For example, when human iPSC were transfected with plasmids expressing the Cas9 nuclease and a single guide RNA (sgRNA), significantly more cells died compared to hiPSC controls that received no sgRNA (Byrne et al., 2015). Both human iPSC and embryonic stem cells (hESC) are especially poised to undergo programmed cell death in response to DNA damage compared to their differentiated progeny or other adult stem cell types, and they undergo high rates of spontaneous apoptosis even during routine culture (Garcia et al., 2014; Grandela et al., 2007; Liu et al., 2014; Qin et al., 2007). This sensitivity also limits the generation of iPSC lines, as blocking the principal DNA damage mediator p53 greatly enhances reprogramming efficiency (Zhao et al., 2008). Accumulation of p53 following DNA damage caused hESC apoptosis through the mitochondrial pathway (rather than p53 transcriptional activation) and knocking down p53 prevented cell death (Grandela et al., 2007; Liu et al., 2013; Qin et al., 2007). Unlike differentiated cells, which activate the pro-apoptotic Bcl-2 family member Bax in the cytosol to form pores in the outer mitochondrial membrane, hESC normally maintain Bax in the active conformation where it is sequestered at the Golgi (Dumitru et al., 2012). DNA damage-induced apoptosis in hESC was Bax-dependent (but Bak-independent), and the active Bax in hES cells translocated to the mitochondria through a p53-dependent mechanism (Dumitru et al., 2012). Human ESC also possess higher mitochondrial priming for apoptosis (the balance of pro-apoptotic and anti-apoptotic Bcl-2 family members), compared to their differentiated progeny (Liu et al., 2013).

There is, therefore, a need for improved methods of engineering genetic changes in hiPSC using CRISPR/Cas9.

BRIEF DESCRIPTION OF THE DRAWINGS

FIG. 1A. A human iPSC line containing a doxycycline-inducible Cas9 nuclease was infected with lentivirus that constitutively expresses CFP together with an sgRNA. Three days after infection, each culture was divided into several wells and treated with the indicated concentrations of doxycycline for up to 14 days. FIG. 1B. At the indicated time points, the percent of CFP$^+$ of live single cells was determined by flow cytometry. Two sgRNAs targeted the coding region of human genes (THY1 and POU5F1) and two control sgRNAs did not target anywhere in the human genome (Negative sgRNA #1 and 2). FIG. 1C. 14 days after doxycycline induction, iPSC infected with the Thy1 sgRNA were stained for expression of the Thy1 surface marker and analyzed by flow cytometry. The percent of Thy1-negative edited cells gated on the CFP$^+$ infected cells is shown for varying concentrations of doxycycline. Results are representative of three independent experiments.

FIG. 2A. Human iPSC containing a doxycycline-inducible Cas9 nuclease were infected with two lentiviruses: one that constitutively expresses CFP together with an sgRNA and another that constitutively expresses EGFP together with an anti-apoptotic gene separated by an IRES sequence. Two sgRNAs targeted the coding region of human genes, THY1 and BSG (CD147), together with a negative control sgRNA. The anti-apoptotic genes tested were a dominant negative form of p53, Bcl-2, Bcl2A1, Bcl-x$_L$, and Mcl-1, together with an EGFP only negative control. Three days after infection, each culture was divided into several wells and treated with 0 or 200 ng/ml doxycycline for up to 6 days. At the indicated time points, the percent of CFP EGFP$^+$ iPSC was determined by flow cytometry. FIG. 2B. The percent of decline of CFP EGFP$^+$ cells after 6 days of doxycycline induction relative to uninduced cultures is shown. Results are representative of three independent experiments.

FIG. 3A. Mouse Thy1 gene targeting scheme. Two Crispr sgRNAs target human THY1 either within intron 1 (Left) or after the polyadenylation site (Right). The mouse Thy1 targeting vector plasmid contains mThy1 coding exons 2 and 3, flanked by hThy1 homology arms outside the sgRNA sites—coding exon 1 (which encodes the signal peptide) is retained but the sgRNA sites are disrupted. FIG. 3B. Plain human iPSC were infected with lentivirus that constitutively expresses EGFP together with an anti-apoptotic gene separated by an IRES. Three days after infection, each culture was nucleofected with plasmids encoding the mThy1 targeting vector, Cas9 nuclease, and Thy1 Left, Right, both, or no sgRNAs (pUC19). Five days later, cells were analyzed by flow cytometry. FIG. 3C. Representative FACS plots gated on live single cells: iPSC from each transfected culture were gated based on EGFP expression and the percentage of cells within those subsets that have gained mThy1 expression and/or lost hThy1 expression are indicated. Using one sgRNA (top row), iPSC that are mThy1$^+$ and hThy1$^-$ have undergone targeted gene replacement at both alleles (*). Using both sgRNAs (bottom row), iPSC that are hThy1$^-$ and mThy1$^-$ have undergone a gene excision or inversion at both alleles (•). The amount of increase between the EGFP negative and positive subset is indicated. FIG. 3D. Left, compiled results showing the fold increase of HR-mediated gene targeting with one or both sgRNAs for all of the anti-apoptotic genes tested: DN p53, Bcl-2, Bcl2A1, Bcl-x$_L$, and Mcl-1; Right, compiled results showing the fold increase of NHEJ-mediated gene deletion with both sgRNAs for all of the anti-apoptotic genes tested. Results are representative of two independent experiments.

FIGS. 4A-D. Bcl-2 overexpression increases HR-mediated gene targeting in human iPSC when transiently transfected with the Cas9 nuclease. FIG. 4A. Mouse Thy1 gene targeting scheme. FIG. 4B. Plasmids were constructed to constitutively express Cas9 together with an anti-apoptotic gene (separated by an IRES) under the constitutively active EF1α promoter. Plain human iPSC were nucleofected with 0.5 µg of one of these Cas9 plasmids together with 2 µg of the mThy1 targeting vector and 1.5 µg of plasmids expressing the Thy1 Left, Right, both, or no sgRNAs (pUC19). Five days later, cells were analyzed by flow cytometry. FIG. 4C. Flow cytometry staining for mThy1 and hThy1 for the Cas9 only sample gated on live single cells; the percent of cells in each quadrant is indicated. No gene targeting was seen in cells transfected with the pUC19 empty vector. FIG. 4D. Compiled gene editing frequencies. The percent of mThy1$^+$ hThy1$^-$ (bottom portion of each bar in the left, center, and right grafts), mThy1$^+$hThy1$^+$ (top portion of bars in the left and center graphs), and mThy1$^-$hThy1$^-$ (top portion of bars in the right graph) cells is graphed for each indicated sample. Lines mark the percentages for the Cas9 only sample. Results are representative of two independent experiments.

FIGS. 5A-B. Bcl-2 overexpression enables double homozygous targeted gene replacement in human iPSC. FIG. 5A. Mouse Thy1 gene targeting scheme (left). Mouse CD147 gene targeting scheme (right): Two sgRNAs target human BSG (CD147) within intron 1 (Left) or after the polyadenylation site (Right). The mouse CD147 targeting vector plasmid contains mCD147 coding exons 2-7, flanked by hCD147 homology arms outside the sgRNA sites—coding exon 1 (which encodes the signal peptide) is retained but the sgRNA sites are disrupted. FIG. 5B. Plain human iPSC were transfected with 1 µg each of the mThy1 and mCD147 targeting vectors together with a total of 2 µg "Cas9 only sgRNA" or "Cas9 Bcl-2 sgRNA" expression plasmid. Cells were transfected with the following sgRNA combinations: Thy1 Left and CD147 Left, Thy1 Right and CD147 Right, all four Thy1 and CD147 sgRNAs, or Negative sgRNA #1. Nine days later, cells were analyzed by flow cytometry for mThy1, hThy1, mCD147, and hCD147 expression. Upper two plots show the percent of Thy1 or CD147 gene replacement as gated on all live single iPSC. Lower four plots show the percent of CD147 gene replacement as gated on the Thy1 gene targeting quadrants. Results are representative of four independent experiments.

FIGS. 6A-C. Bcl-2 overexpression increases the efficiency of engineering single base pair changes using ssODN donors in human iPSC. FIG. 6A. A sgRNA was designed to target exon 14 of human JAK2. The V617F mutation was encoded within 110 bp ssODN donors (in either the plus or minus orientation) or a plasmid containing 1.9 kb and 1.3 kb flanking homology arms. Small triangles indicate the primer sites for the genotyping PCR reaction outside the ssODN sequence. Plain human iPSC were transfected with 2 µg "Cas9 only sgRNA" or "Cas9 Bcl-2 sgRNA" expression plasmid and/or 10 µM ssODN or 2 µg V617F plasmid donor. 17 days later, cells were harvested for genomic DNA purification. The genomic region around exon 14 was PCR amplified and analyzed by MiSeq. FIG. 6B. Representative sequencing results for the "Cas9 Bcl-2 sgRNA" expression plasmid with the V617F plasmid donor. The percent of MiSeq reads containing the Jak2 V617F mutation (HR) or indel mutations (NHEJ) is indicated together with a plot of bp position along the PCR product versus the number of sequencing reads. FIG. 6C. Compiled HR and NHEJ frequencies for all the samples and an untransfected control. Results are representative of two independent experiments. Jak2 sgRNA, nucleotides 2-24 of SEQ ID NO:12; ssODNs: SEQ ID NO:21 (+) and SEQ ID NO:22 (−). The sequence ttttaaattatggagtatgtttctgtggagacgagagtaa is nucleotides 41 to 78 of SEQ ID NO:21. The sequence aaaatttaatacctcatacaaagacacctctgctctcatt is the reverse complement of nucleotides 41-78 of SEQ ID NO:21.

FIG. 8A. Plasmids were constructed to constitutively express the Cas9 nuclease with a form of Bcl-2 (separated by an IRES), and a sgRNA. Three human iPSC lines were nucleofected with 2 µg of mThy1 or mCD147 targeting vector and 2 µg of "Cas9 sgRNA" or "Cas9 Bcl-2 sgRNA" expression plasmid. 5-9 days later, cells were analyzed by flow cytometry. FIG. 8B. Mouse Thy1 gene targeting scheme. FIG. 8C. Single amino acid mutations were generated for the Bcl-2 BH1

(G145A) or BH4 (Y28A) domains. Compiled gene editing frequencies for cells transfected with the Left, Right, or Both Thy1 sgRNAs. The percent of mThy1$^+$hThy1$^-$ (bottom portion of each set of bars in each graph), mThy1$^+$hThy1$^+$ (top portion of left and center sets of bars in each graph and center portion of right set of bars in each graph), and mThy1$^-$hThy1$^-$ (top portion of right set of bars in each graph) cells among the various samples is indicated. FIG. 8D. Mouse CD147 gene targeting scheme. FIG. 8E. Flow cytometry staining for mCD147 and hCD147 for retrovirally-derived PGP1 hiPSC transfected with "Cas9 sgRNA" or "Cas9 Bcl-2 sgRNA". Samples are gated on live single cells; the percent of cells in each quadrant is indicated. FIG. 8F. Compiled gene editing frequencies for cells transfected with the Left, Right, or both CD147 sgRNAs. The percent of mCD147$^+$hCD147$^-$ (bottom portion of each set of bars in each graph), mCD147$^+$hCD147$^+$ (top portion of left and center sets of bars in each graph and center portion of right set of bars in each graph), and mCD147$^-$hCD147$^-$ (top portion of right set of bars in each graph) cells among the three hiPSC lines is indicated.

FIG. 9A. Mouse Thy1 gene targeting scheme. Human iPSC were nucleofected with the mThy1 targeting vector system plasmids and analyzed by flow cytometry five days later. The percentages of mThy1$^+$hThy1$^-$, mThy1$^+$hThy1$^+$, and mThy1$^-$hThy1$^-$ cells for each sample (gated on live single cells) are graphed. Lines mark the percentage values for the control sample. FIGS. 9B-9D. Human iPSC were nucleofected with: 2 µg mThy1 targeting vector; 0.5 µg Cas9 plasmid; and 1.5 µg of sgRNA plasmids. The sample was divided into multiple wells and cultured in plain media (mTeSR1+10 µM Y-27632 ROCK inhibitor) supplemented with the indicated chemical inhibitor for three days. 20 µM pifithrin α, 200 µM peptide V5 (VPMLK, SEQ ID NO:31), 200 µM peptide control (IPMIK, SEQ ID NO:32), 50 µM TEMPOL, or the indicated concentrations of SCR7 or L755507 were used. FIG. 9B, mThy1$^+$hThy1$^-$ (bottom portion of each bar in each graph), mThy1$^+$hThy1$^+$ (top portion of each bar in each graph). FIG. 9C, mThy1$^+$hThy1$^-$ (bottom portion of each bar in each graph), mThy1$^+$hThy1$^+$ (top portion of each bar in left and center graphs, middle portion of each bar in right graph), and mThy1$^-$hThy1$^-$ (top portion of each bar in right graph). FIG. 9D, mThy1$^+$hThy1$^-$ (bottom portion of each bar in each graph), mThy1$^+$hThy1$^+$ (center portion of each bar in each graph), and mThy1$^-$hThy1$^-$ (top portion of each bar in each graph). FIGS. 9E-9F. Human iPSC were nucleofected with: 2 µg mThy1 targeting vector plasmid; 0.5 µg Cas9 plasmid; 1 µg of sgRNA plasmids; and 0.5 µg of plasmid expressing the indicated DNA repair gene or pUC19 control ("Cas9 only"). For FIG. 9E, cultures were treated with 50 µM zVAD and 10 µM SB203580 post transfection. mThy1$^+$hThy1$^-$ (bottom portion of each bar in each graph), mThy1$^+$hThy1$^+$ (top portion of each bar in left and center graphs, middle portion of each bar in right graph), and mThy1$^-$hThy1$^-$ (top portion of each bar in right graph). FIG. 9F, mThy1$^+$hThy1$^-$ (bottom portion of each bar in each graph), mThy1$^+$hThy1$^+$ (top portion of each bar in left and center graphs, middle portion of each bar in right graph), and mThy1$^-$hThy1$^-$ (top portion of each bar in right graph). FIG. 9G. Human iPSC were nucleofected with: 2 µg mThy1 targeting vector plasmid; 0.5 µg Cas9 plasmid; and 1.5 µg of sgRNA plasmids. The indicated viral inhibitor genes were cloned into the Cas9 expression vector following an IRES sequence. Cultures were supplemented with 50 µM zVAD post transfection. mThy1$^+$hThy1$^-$ (bottom portion of each bar in each graph), mThy1$^+$hThy1$^+$ (top portion of each bar in left and center graphs, middle portion of each bar in right graph), and mThy1$^-$hThy1$^-$ (top portion of each bar in right graph).

FIG. 10A and FIG. 10B. Mouse Thy1 gene targeting scheme. Human iPSC were nucleofected with the mThy1 targeting vector, Cas9 nuclease, and Thy1 sgRNA expressing plasmid or pUC19 empty vector. Nucleofected cells were evenly divided and plated onto plain media (mTeSR1+10 µM Y-27632 ROCK inhibitor), or media supplemented with the indicated chemical inhibitor. For specific caspase inhibitors, the principal caspase they target is noted in parentheses. As observed in previous reports, most of the nuclease-mediated cell death occurred between days 1-2 post transfection, and the proportions of mThy1$^+$ cells remained stable beyond day 5. FIG. 10C. Two days after nucleofection, viable cells were counted. Error bars indicate s.e.m. of technical duplicates. Lines mark the count levels for nucleofected cells in plain media with or without sgRNA. FIG. 10D. Five days after transfection, cells were analyzed by flow cytometry for mThy1 and hThy1 expression. The percent of mThy1$^+$hThy1$^-$ (bottom of each bar) and mThy1$^+$hThy1$^+$ (top of each bar) cells of live single cells is indicated. Lines mark the levels for cells in plain media. No gene targeting was seen in cells transfected with the pUC19 empty vector. FIG. 10E. FACS plots of human iPSC transfected with the mThy1 targeting vector, Cas9 nuclease, and Thy1 Left and Right sgRNAs. Cells were subsequently cultured for 5 days in plain media±50 µM zVAD and ±10 µM SB203580. FIG. 10F. Human iPSC cultures were single cell FACS sorted into 96-well tissue culture plates containing a MEF feeder layer and hES media supplemented with SMC4 inhibitors±50 µM zVAD for eight days. Ten days after sorting, the number of surviving iPSC colonies was counted (from 190 cells sorted). PGP1 hiPSC lines created using retroviral vectors or non-integrating methods were both tested.

FIGS. 11A-C. Genotype and pluripotency of targeted mThy1 mCD147 hiPSC clones. FIG. 11A. Mouse Thy1 and mouse CD147 gene targeting schemes from FIG. 5. Small triangles indicate the primer sites for the ten genotyping PCR reactions. Single hiPSC were FACS sorted into individual wells and cultured. FIG. 11B. After clonal expansion, hiPSC lines were analyzed by flow cytometry for mThy1, hThy1, mCD147, and hCD147 expression (top panels). Genomic DNA was extracted and genotyped using the ten PCR reactions (bottom panels). Alleles were identified based on the size of the PCR products: native human (h); recombined mouse (m); or excised between the two sgRNA sites (Δ). Data from representative clones is shown from samples transfected with Thy1 and CD147 Left sgRNAs or all four sgRNAs. FIG. 11C. Targeted, sorted, and expanded hiPSC clones were analyzed by flow cytometry for expression of the pluripotency markers Tra-1/60 and Oct3/4. Shaded peaks indicate the background staining from an isotype control antibody.

FIG. 13. Nuclease-mediated toxicity in human iPSC can be rescued by a short hairpin RNA (shRNA) construct to knockdown p53 expression.

DETAILED DESCRIPTION

Figure 1A:
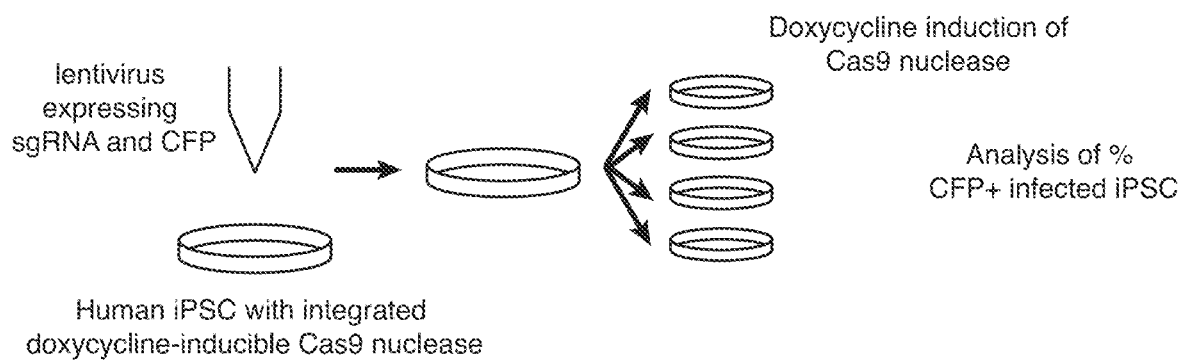
FIGS. 1A-C. Cas9 nuclease toxicity in human iPSC only occurs with sgRNAs that target the human genome.

CRISPR/Cas9 nuclease toxicity severely limits gene editing in human pluripotent stem cells (hiPSC). This disclosure provides methods of reducing this toxicity and improving gene targeting frequencies in such hiPSC and in other types of stem cells by inhibiting p53 or Bax. This inhibition can be achieved, for example, by expressing an anti-apoptosis protein or by using genetic or chemical agents to reduce expression of p53 or Bax or to inhibit the function of p53 or Bax.

This disclosure also provides methods of increasing gene targeting frequencies several-fold by overexpressing Bcl-2 with Cas9 during a transient transfection to increase gene targeting frequencies several-fold. For example, base pair changes with 39% homologous recombination efficiency or multiplex gene replacements can be achieved using a simple plasmid transfection without antibiotic selection. Increasing the absolute gene targeting frequency reduces the need for an antibiotic selection marker that must subsequently be removed through a second round of culture and cloning, which adds extra passages and cost and risks contamination or loss of pluripotency. These advances can be used in conjunction with other rapidly developing CRISPR technologies, including improvements in specificity, other types of nucleases, and further enrichment, screening, and selection schemes. Thus, the methods described herein improve the use of genetically modified stem cells, particularly hiPSC, for both experimental studies and therapeutic purposes (e.g., tissue engineering).

Genetically Modified Stem Cells

This disclosure provides genetically modified stem cells and methods of editing the genome of stem cells such that populations of these cells can be used as in vitro model system or for in vivo therapeutic purposes.

The stem cell to be genetically modified can be an embryonic stem cell (ESC) or a somatic stem cell such as hiPSC, a hematopoietic stem cell, a neural stem cell, or a mesenchymal stem cell. In some variations, the genetically modified stem cell is human. In other variations, the stem cell is that of a non-human mammal, such as a non-human primate, a mouse, or a rat. Methods of obtaining and growing various types of stem cells are well known the in the art (e.g., Takahashi et al., 2007; Yu et al., 2007; Robinton & Daley, 2012; Drawnel et al., 2014; Li et al., 2015; US 2012/0087933; US 2014/0377865; US 2015/0299712; US 2015/0307841; US 2016/0032250; US 2016/0060594).

The genetically modified stem cells comprise (a) an expression construct encoding a programmable DNA nuclease or a meganuclease; and (b) an anti-apoptosis component. A "programmable DNA nuclease" as used herein means a DNA nuclease that can be engineered to recognize and cleave a desired sequence in the genome of the stem cell. Examples of a programmable DNA nuclease include a class 2 clustered regularly-interspaced short palindromic repeat (CRISPR) nucleases, a zinc finger nuclease (ZFN), and a Transcription Activator-Like Effector nuclease (TALEN). Each of these types of programmable DNA nucleases is well known in the art.

Particular examples of a CRISPR nuclease include a CRISPR associated protein 9 (Cas9) nuclease, a CRISPR from *Prevotella* and *Francisella* 1 nuclease (Cpf1), a Class 2 candidate 1 nuclease (C2c1), a Class 2 candidate 2 nuclease (C2c2), and a Class 2 candidate 3 nuclease (C2c3).

"Cas9 nucleases" exist in many bacteria, including *S. pyogenes*, *S. thermophilus*, and *Neisseria meningitidis*. A "Cas9 nuclease" includes a Cas9 nuclease with native (or wild-type) nuclease activity, as well as modified versions of a Cas9 nuclease, such as SpCas9-HF1 ("high fidelity variant number 1;" Kleinstiver et al., 2016), eSpCas9 ("enhanced specificity Cas9;" Slaymaker et al., 2016), Cas9 nickases (e.g., Cong et al., 2013; Mali et al., 2013) and nuclease-deficient or nuclease-null Cas9 (e.g., Jinek et al., 2012) fused to a nuclease domain (e.g., FokI).

Examples of meganucleases include I-SceI meganuclease and I-CreI meganuclease, as well as engineered derivatives thereof (e.g., Thermes et al., 2002; Arnould et al., 2011).

An "anti-apoptosis component" as used herein is a component that inhibits the apoptotic function of p53 or Bax.

In some variations, the anti-apoptosis component is an anti-apoptosis protein, such as a dominant negative mutant of p53, or a genetic mediator which binds to p53 or promotes its degradation including, but not limited to, mouse double minute 2 homolog (MDM2), p53-induced protein with a RING (Really Interesting New Gene)-H2 domain (Pirh2, RCHY1), constitutively photo-morphogenic 1 (COP1), and ARF (Alternative Reading Frame) Binding Protein 1 (ARF-BP1, HUWE1). See, e.g., Tsvetkov et al., "2010; Pant & Lozano, 2014.

In some variations, the anti-apoptosis component is an anti-apoptosis protein, such as a member of the Bcl-2 family, such as B cell lymphoma 2 protein (Bcl-2), Bcl-2-related protein A (Bcl2A1), B-cell lymphoma-extra large protein (Bcl-$x_L$), myeloid cell leukemia 1 protein (Mcl-1), B cell lymphoma 2-like protein 2 (Bcl-w), or Bcl-2-like protein 10 (Bcl-B).

In some variations, the anti-apoptosis component is an oligonucleotide inhibitor of p53, such as an shRNA.

In some variations, the anti-apoptosis component is a small molecule Bax channel blocker, such as Bax channel inhibitor-1 (Bci1) and Bax channel inhibitor-2 (Bci2) (Hetz et al., 2005):

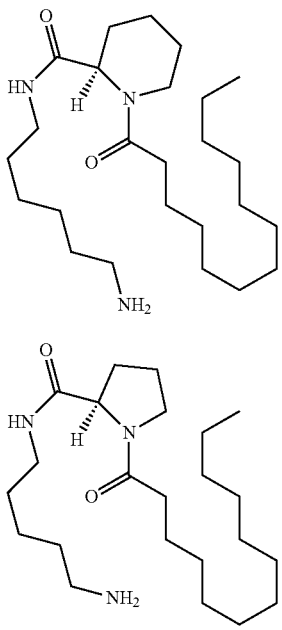

In some variations, the genetically modified stem cell also comprises an sgRNA (single guide RNA) complementary to a target nucleic acid sequence of the stem cell genome. The genetically modified stem cell may comprise multiple such sgRNAs, each complementary to a different target nucleic acid sequence of the stem cell genome. In some variations in which the programmable DNA nuclease is a CRISPR nuclease, the expression construct encoding the CRISPR nuclease also includes a nucleic acid encoding one or more sgRNAs. In other variations, one or more sgRNAs can be provided using one or more separate expression constructs. Types of sgRNAs are well known in the art (e.g., US 2014/0356959; US 2015/0259704).

This disclosure also provides methods of making a genetically modified stem cell. In some variations, an expression construct encoding a Cas9 nuclease and Bcl-2 is provided to a stem cell. In some of these variations, the expression construct also encodes one or more sgRNA.

In some variations, (a) an expression construct encoding a programmable DNA nuclease and (b) an expression construct encoding an anti-apoptosis protein (e.g., a DN p53, Bcl-2, Bcl2A1, Bcl-$x_L$, Mcl-1), an oligonucleotide inhibitor of p53 (e.g., shRNA), or a Bax channel blocker is provided to a stem cell.

In other variations, a stem cell comprises an expression construct encoding a programmable DNA nuclease, and the method comprises provided to the stem cell an expression construct encoding an anti-apoptosis protein (e.g., a DN p53, Bcl-2, Bcl2A1, Bcl-$x_L$, Mcl-1), an oligonucleotide inhibitor of p53 (e.g., shRNA), or a Bax channel blocker.

Expression constructs useful for the expression of Cas9, anti-apoptosis proteins, and sgRNA are described in the Examples, below, but any suitable expression construct can be used.

Methods of delivering exogenous nucleic acids to stem cells are well known in the art and include plasmid vectors, viral vectors (e.g., lenti-, adeno-, and adeno-associated viral vectors), and ribonucleoproteins. See Shui et al., 2016. Nucleic acids can also be delivered by electroporation, injection, or lipofection. The nucleic acid encoding the programmable DNA nuclease or meganuclease and the nucleic acid encoding an anti-apoptosis protein can be provided in separate expression constructs or the same expression construct.

This disclosure also provides methods of altering a target nucleic acid sequence of a stem cell, comprising providing a genetically modified stem cell as described above with a single guide RNA (sgRNA) complementary to a target nucleic acid sequence of the stem cell genome or with a plurality of sgRNA complementary to a plurality of target nucleic acid sequences of the stem cell genome, i.e., to carry out multiplex editing of the stem cell genome. sgRNA can be delivered to the stem cell by methods well known in the art. Plasmid donors with >1 kb homology arms for small changes (1-100 bp) are particularly useful.

In some variations, the genetically modified stem cell is also contacted with a caspase inhibitor (e.g., zVAD-fmk) to reduce dissociation-mediated cell death, particularly following transfection or cell sorting, and/or a p38 MAP kinase inhibitor (e.g., SB203580) to enhance gene targeting efficiency; see Example 5, below.

Expression Constructs Encoding a Cas9 Nuclease and Bcl-2

This disclosure also provides an expression construct encoding a Cas9 nuclease and Bcl-2. Expression constructs useful for the expression of a Cas9 nuclease and Bcl-2 are described in the Examples, below, but any suitable expression construct can be used. In some variations, the expression construct also encodes a single guide RNA (sgRNA) or a plurality of sgRNAs.

The following examples are intended to illustrate but not limit this disclosure.

Example 1

Experimental Procedures

DNA constructs. Sequences of sgRNAs are provided in the table below. Bold indicates a base that was changed to a G to enable transcription from the U6 promoter. PAM sequences for the sgRNA targeting site are underlined where applicable.

|  |  | SEQ ID NO: |
|---|---|---|
| THY1 (coding exon) | GGGTC AGGCT GAACT CGTAC <u>TGG</u> | 1 |
| THY1 truncated | GTC AGGCT GAACT CGTAC <u>TGG</u> | 2 |
| POU5F1 (coding exon) | GCTGG AGCAA AACCC GGAGG <u>AGG</u> | 3 |
| Negative sgRNA #1 | G CTTCA AAGAA CGGCG CTAAC | 4 |
| Negative sgRNA #2 | G GAGAC GATTA ATGCG TCTCG | 5 |
| CD147 (coding exon) | GTCGT CAGAA CACAT CAACG <u>AGG</u> | 6 |
| CD147 truncated | GCGT CAGAA CACAT CAACG <u>AGG</u> | 7 |
| THY1 Left | GCACA GTCTC AGAAA AGCGC AGG | 8 |

-continued

| | | SEQ ID NO: |
|---|---|---|
| THY1 Right | GTTAG TAGCA ACGCT ACCCC AGG | 9 |
| CD147 Left | G ATTTC CTGCG CTGAA TCGGG TGG | 10 |
| CD147 Right | G TGGCT CCTGT CTGTG CCTGA CGG | 11 |
| Jak2 | G AATTA TGGAG TATGT GTCTG TGG | 12 |
| HLA-A | GGACC TGCGC TCTTG GACCG CGG | 13 |
| HLA-A truncated | GACC TGCGC TCTTG GACCG CGG | 14 |
| HLA-B or C | GGGCC GCCTC CCACT TGCGC TGG | 15 |
| HLA-B or C truncated | GCC GCCTC CCACT TGCGC TGG | 16 |

The mouse Thy1 and CD147 gene targeting systems and the original plasmids to constitutively express the EF1α promoter-Cas9 nuclease or the U6 promoter-sgRNA have been previously described and verified (Byrne et al., 2015). The Jak2 V617F 110 bp ssODN, Construction of the Plasmid Donor, and Sequencing Primers.

PCR reactions were done using polymerase sold under the trademark KAPA HIFI™ HotStart polymerase; primers and double-stranded DNA fragments sold under the trademark GBLOCKS® are from IDT. Plasmids were constructed using isothermal assembly, transformed into Stbl3 competent E. coli (Invitrogen), grown at 30° C., and verified by Sanger sequencing (Genewiz). Anti-apoptotic genes were obtained from previously published plasmids: Bcl-2 (Addgene plasmid #8793) and Bcl-$x_L$ (#8790) (Cheng et al., 2001); Bcl2A1 (#36973) (Pratt et al., 2012); and Mcl-1 (#21605) (Maurer et al., 2006). The dominant negative p53 sequence from Addgene plasmid #9058 (Hahn et al., 2002) was synthesized as a gBlock. These genes were cloned into the EF1α promoter-Cas9 nuclease plasmid after an IRES.

Mutations to the Bcl-2 gene were made using the site-directed mutagenesis kit sold under the trademark QUIKCHANGE® Lightning Site-Directed Mutagenesis kit (Stratagene) using the following primers:

Y28A:
(SEQ ID NO: 17)
5' GTCGCAGAGGGGCGCCGAGTGGGATGCG 3'

(SEQ ID NO: 18)
5' CGCATCCCACTCGGCGCCCCTCTGCGAC 3'

G145A:
(SEQ ID NO: 19)
5' AGGCCACAATCCTCGCCCAGTTCACCCCG 3'

(SEQ ID NO: 20)
5' CGGGGTGAACTGGGCGAGGATTGTGGCCT 3'

Other modifier genes were obtained from previously published plasmids: BRCA1 (Addgene plasmid #14999) (Cortez et al., 1999); BRCA2 (#16246) (Wang et al., 2002); and Trex2 (#40210) (Certo et al., 2012; Chari et al., 2015). CtIP (RBBP8) was cloned from human ORFeome v8.1 (horfdb.dfci.harvard.edu clone #1563) (ORFeome Collaboration, 2016) and altered from UniprotKB isoform Q99708-2 to Q99708-1. Rad51 (CCDS10062.1) and MRE11A (CCDS8299.1) were synthesized as double-stranded DNA fragments sold under the trademark GBLOCKS® (IDT). These genes were cloned in the constitutive expression plasmid (Byrne et al., 2015), after the EF1α promoter, replacing the Cas9 nuclease. E1B55K, and E4orf6 (Chu et al., 2015) were synthesized as double-stranded DNA fragments sold under the trademark GBLOCKS® (IDT), and inserted into the constitutive expression plasmid, after the EF1α promoter, Cas9 nuclease, and an IRES.

The U6 promoter-sgRNA (for each sgRNA sequence) was cloned into the EF1α promoter-Cas9 nuclease or EF1α promoter-Cas9 nuclease-IRES-Bcl-2 expression plasmids to form the "Cas9 only sgRNA" or "Cas9 Bcl-2 sgRNA" plasmids used in Examples 6 and 7.

Jak2 V617F Targeting Vectors.

Desalted 110 bp ssODN (IDT) encoding the Jak2 V617F mutation were ordered in the plus (SEQ ID NO:21) or minus (SEQ ID NO:22) orientation. For the Jak2 V617F plasmid targeting vector, homology arms were PCR amplified from purified PGP1 human genomic DNA (upstream, SEQ ID NO:23 and SEQ ID NO:24; downstream, SEQ ID NO:25 and SEQ ID NO:26) and cloned using isothermal assembly into the pUC19 plasmid backbone (amplified with SEQ ID NO:27 and SEQ ID NO:28).

SEQ ID NO: 21
5' AAGTATGATGAGCAAGCTTTCTCACAAGCATTTGGTTTTAAATTA
TGGAGTATGTTTCTGTGGAGACGAGAGTAAGTAAAACTACAGGCTTTC
TAATGCCTTTCTCAGAG 3'

SEQ ID NO: 22
5' CTCTGAGAAAGGCATTAGAAAGCCTGTAGTTTTACTTACTCTCGT
CTCCACAGAAACATACTCCATAATTTAAAACCAAATGCTTGTGAGAAA
GCTTGCTCATCATACTT 3'

SEQ ID NO: 23
5' GTGCAGGCTTTCAACAATTACTTTG 3'

SEQ ID NO: 24
5' TCTCGTCTCCACAGAAACATACTCCATAATTTAAAACC 3'

SEQ ID NO: 25
5' ATTATGGAGTATGTTTCTGTGGAGACGAGAGTAAGTAAAAC
TACAG 3'

SEQ ID NO: 26
5' ATCTTGCTCTAGATTGGGCTTTGG 3'

SEQ ID NO: 27
5' CTTGAGCCAAAGCCCAATCTAGAGCAAGATTAGACGTCAGGTGGC
ACTTTTC 3'

SEQ ID NO: 28
5' CTTTACAAAGTAATTGTTGAAAGCCTGCACGTTTGCGTATTGGGC
GCTCTTC 3'

Stem Cell Culture.

Verified human iPSC (retrovirally-reprogrammed) from Personal Genome Project donors PGP1 and PGP4 were obtained through the Coriell Institute Biorepository at passage 20 (#GM23338, GM23340) (Ball et al., 2012; Byrne et al., 2015; Lee et al., 2009). The non-integrated PGP1 hiPSC line was generated from PGP1 fibroblasts using the Sendai virus-based reprogramming kit sold under the trademark CYTOTUNE® iPS Reprogramming kit (Invitrogen) and received at passage 4. All three lines were adapted to feeder-free culture conditions, karyotyped, and FACS stained for expression of pluripotency markers. All experiments were done at passage number 29-42 for the retroviral hiPSC lines and passage 9-15 for the non-integrated hiPSC line.

A transposon vector sold under the trademark PIGGYBAC™ vector containing a TRE 3G tetracycline/doxycycline-inducible promoter-Cas9 nuclease and a hEF1 HTLV constitutive promoter-Tet On 3G transactivator-T2A cleavage sequence-Hygromycin resistance insert was combined with a transposase expression plasmid, nucleofected into PGP1 (retroviral) hiPSC, and selected with hygromycin, similar to (Chavez et al., 2015).

Cell lines were maintained on solubilized basement membrane matrix secreted by Engelbreth-Holm-Swarm (EHS) mouse sarcoma cells sold under the trademark MATRIGEL®-coated plates (BD) and grown in feeder-free cell culture medium sold under the trademark MTESR1™ (Stem Cell Technologies) according to standard protocols. 10 µM of the ROCK inhibitor Y-27632 (R&D Systems, Abcam) was added to the culture before, during, and after passaging with a cell detachment solution sold under the trademark ACCUTASE® (EMD Millipore) or after passaging with an enzyme-free passaging reagent sold under the trademark RELESR™ (Stem Cell Technologies).

Stem Cell Verification.

Pluripotency of iPSC cultures was verified by flow cytometry staining using anti-human Tra-1/60 PE (TRA-1-60, BD) and anti-human Oct3/4 eFluor 660 (EM92, eBioscience) with the fixation buffer sold under the trademark BD CYTOFIX™ and permeabilization buffer sold under the trademark PHOSFLOW™ Perm/Wash buffers. Human g-band karyotype analysis was done by Cell Line Genetics. Viable cell counts were measured with the cell analyzer sold under the trademark MUSE® Count & Viability Assay kit (EMD Millipore). Anti-human HLA-A2 APC (BB7.2) and anti-human HLA-BC PE (B1.23.2) were purchased from eBioscience. Human iPSC cultures were treated with 50 ng/ml recombinant interferon gamma (eBioscience) for 2 days prior to HLA staining.

Lentiviral Infection.

A U6 promoter-sgRNA and CAGGS promoter-Cerulean fluorescent protein construct was cloned into the pLVX lentiviral vector backbone (Clontech) (pSB700, Addgene #64046). A similar construct containing a U6 promoter-shRNA and CAGGS promoter-EGFP was cloned into the pLVX lentiviral vector backbone. Individual sgRNA or shRNA sequences were cloned into these vectors. The shRNA sequences for human TP53 (#TRCN0000003755) and control (#TRCN0000057023) are from the shRNA library sold under the trademark Sigma MISSION® shRNA library. An EF1α promoter-EGFP-IRES-anti-apoptotic gene construct was also cloned into the pLVX lentiviral backbone. Lentiviral plasmids were combined with psPax2 (Addgene plasmid #12260) and pMD2.G (#12259) and transfected into HEK 293T cells using TransIT-293 transfection reagent (Mirus Bio). 25 µM chloroquine (Sigma) was included in the media for the first 24 hr after transfection. Cell culture supernatants were harvested at 48 and 72 hours, and concentrated using the PEG virus precipitation kit (BioVision). Lentivirus was added to human iPSC for one day in mTeSR1 media with 4 µg/ml polybrene (EMD Millipore) and 10 µM Y-27632. At least three days after infection, cells were treated with doxycycline (Sigma) for the indicated concentrations and times.

Stem Cell Transfection.

Plasmids were purified using the plasmid DNA purification kit sold under the trademark Qiagen ENDOFREE® Plasmid Maxi kit and nucleofected into iPSC cells using the Lonza 4D-Nucleofector X unit (Buffer P3, Program CB-150). For each 20 µl nucleofection reaction, 0.2-0.5×106 iPSC were transfected with up to 4 µg of plasmid DNA. Post-nucleofection, iPSC were plated onto solubilized basement membrane matrix secreted by Engelbreth-Holm-Swarm (EHS) mouse sarcoma cells sold under the trademark MATRIGEL®-coated wells containing feeder-free cell culture medium sold under the trademark MTESR1™ media with 10 µM Y-27632 plus other chemical inhibitors when noted. Later experiments included 50 µM zVAD-fmk (Bachem) for 1 day and 10 µM SB203580 (Biovision) for 4-5 days post transfection (see FIGS. 5, 6, 11, and 12). For FIG. 6 (ssODN transfection), 200 ng/ml recombinant B 18R (eBioscience), was also added to the culture for 5 days post transfection.

Chemical Inhibitors in Stem Cell Culture.

The following inhibitors were added to the hiPSC culture at the concentrations and time periods indicated in the Examples below.

1. p53 or Bax inhibitors: cyclic pifithrin α (StemCell Technologies); pifithrin (Tocris); peptide V5, peptide control, iMAC1 and iMAC2 (EMD Millipore); N-acetyl cysteine and 4-hydroxy TEMPO (TEMPOL) (Sigma).
2. Caspase inhibitors: zVAD-fmk, zVAD(OMe)-fmk, and zD(Ome)E(Ome)VD(Ome)-fmk (Bachem); zVD(Ome)VAD(Ome)-fmk, zVE(Ome)ID(Ome)-fmk, zIE(Ome)TD(Ome)-fmk, zLE(Ome)HD(Ome)-fmk, and zAE(Ome)VD(Ome)-fmk (R&D Systems).
3. HR/NHEJ: SCR7 (Xcess Biosciences); L755507 (Tocris); Brefeldin A (EMD Millipore).

Flow Cytometry. Cells were dissociated using cell dissociation enzyme sold under the trademark TRYPLE™ Express and washed in FACS buffer: PBS+10% fetal calf serum (Invitrogen). The following antibodies were purchased from eBioscience: Anti-human Thy1 APC or PECy7 (eBio5E10), anti-mouse Thy1.2 PE or FITC (30-H12), anti-human CD147 APC (8D12), anti-mouse CD147 PE (RL73). For antibody staining, cells were stained in FACS buffer for 30 min at 4° C. and washed twice in FACS buffer. Cells were finally resuspended in FACS buffer with 20 ng/ml DAPI (Sigma) or 0.5 µM ToPro-3 (Invitrogen) as viability dye and analyzed on a BD flow cytometer sold under the trademark LSRFORTESSA™ flow cytometer. Single-cell hiPSC FACS sorting was done as previously described (Byrne et al., 2015); 50 µM zVAD-fmk was added with the SMC4 inhibitors for eight days after sorting for FIG. 11 and where otherwise indicated.

Next-Generation Sequencing.

The percent of indel or gene targeted mutations at the Jak2 V617F site was assayed using next-generation sequencing (Byrne et al., 2015; Guell et al., 2014). To sequence the Jak2 locus, the first round of PCR was done on purified genomic DNA (genomic DNA purification kit sold under the trademark GENELUTE™ Mammalian Genomic DNA Miniprep Kit, Sigma) using the following primers, in which Illumina adapter sequences are underlined:

```
                                                    SEQ ID NO: 29
5' CTTTCCCTACACGACGCTCTTCCGATCTTTATGGACAACAGTCAA

ACAACAATT 3'

SEQ ID NO: 30
5' GGAGTTCAGACGTGTGCTCTTCCGATCT ACACCTAGCTGTGATC

CTGAAACTG 3'
```

A second round of nested PCR with PCR index primers sold under the trademark NEXTERA™ index primers (Illumina) was used to add barcodes and remaining adaptor sequences. Both PCR reactions were supplemented with fluorescent dye sold under the trademark SYBR® Green (Invitrogen) and monitored on a quantitative PCR machine to prevent over-amplification. PCR products were gel-purified using the PCR purification kit sold under the trademark QIAQUICK® Gel Extraction kit (Qiagen).

Paired-end 150 Illumina MiSeq reactions were analyzed by the CRISPR Genome Analyzer (crispr.med.harvard.edu).

Example 2

Figure 1B:
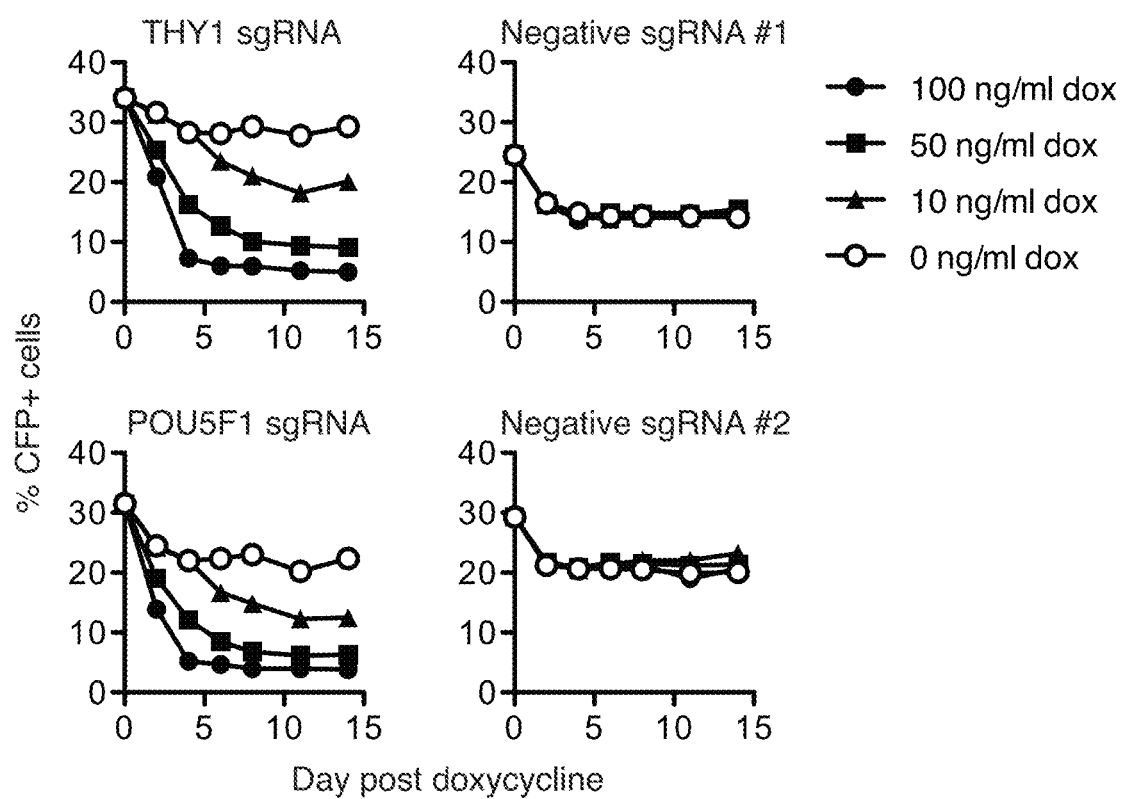
Figure 1C:
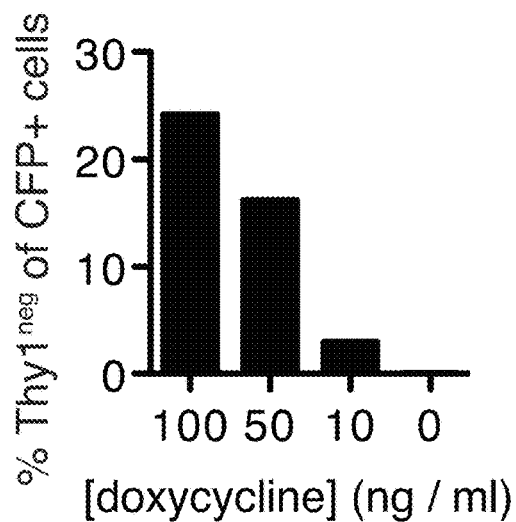

Cas9 Nuclease Activity is Toxic to Human Pluripotent Stem Cells, but can be Rescued by Inhibiting p53 or the Mitochondrial Pathway of Apoptosis A hiPSC line that contains a doxycycline-inducible Cas9 nuclease expression construct was used to study the extent of Cas9 nuclease-mediated death. These cells were infected with lentivirus to constitutively express an sgRNA and a CFP marker, divided into several wells, treated with varying concentrations of doxycycline, and the proportion of CFP$^+$ cells was monitored over two weeks (FIG. 1A). Induction of the Cas9 nuclease produced a dramatic decline in the amount of CFP$^+$sgRNA$^+$ cells, but only with sgRNAs targeting human genes. No decline was seen with negative control sgRNAs designed to not cut anywhere in the human genome (FIG. 1B). Lowering titrations of Cas9 induction over two weeks only yielded lower frequencies of gene disruption (FIG. 1C).

Figure 2A:
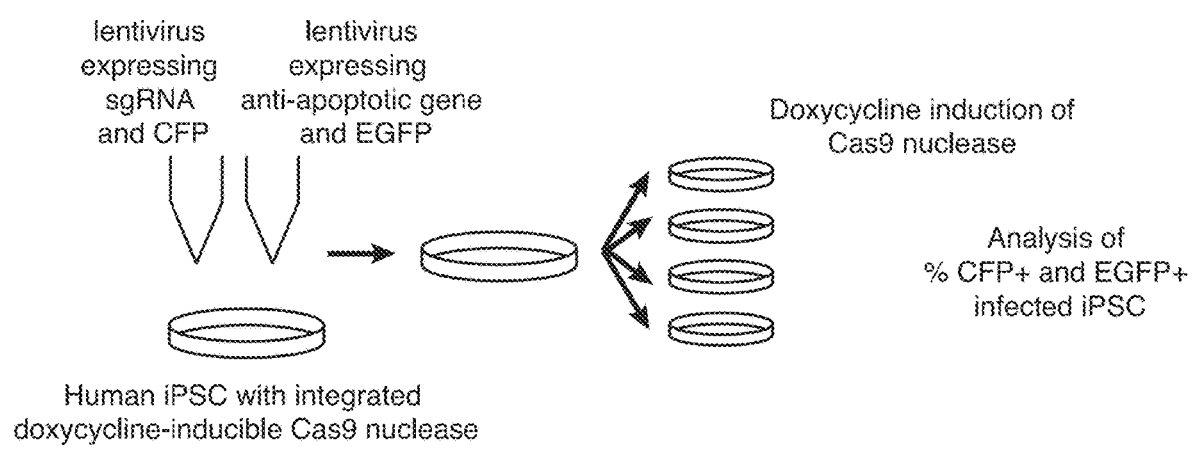
FIGS. 2A-B. Nuclease-mediated toxicity in human iPSC can be rescued by overexpression of dominant negative p53 or anti-apoptotic Bcl-2 family members.
Figure 2B:
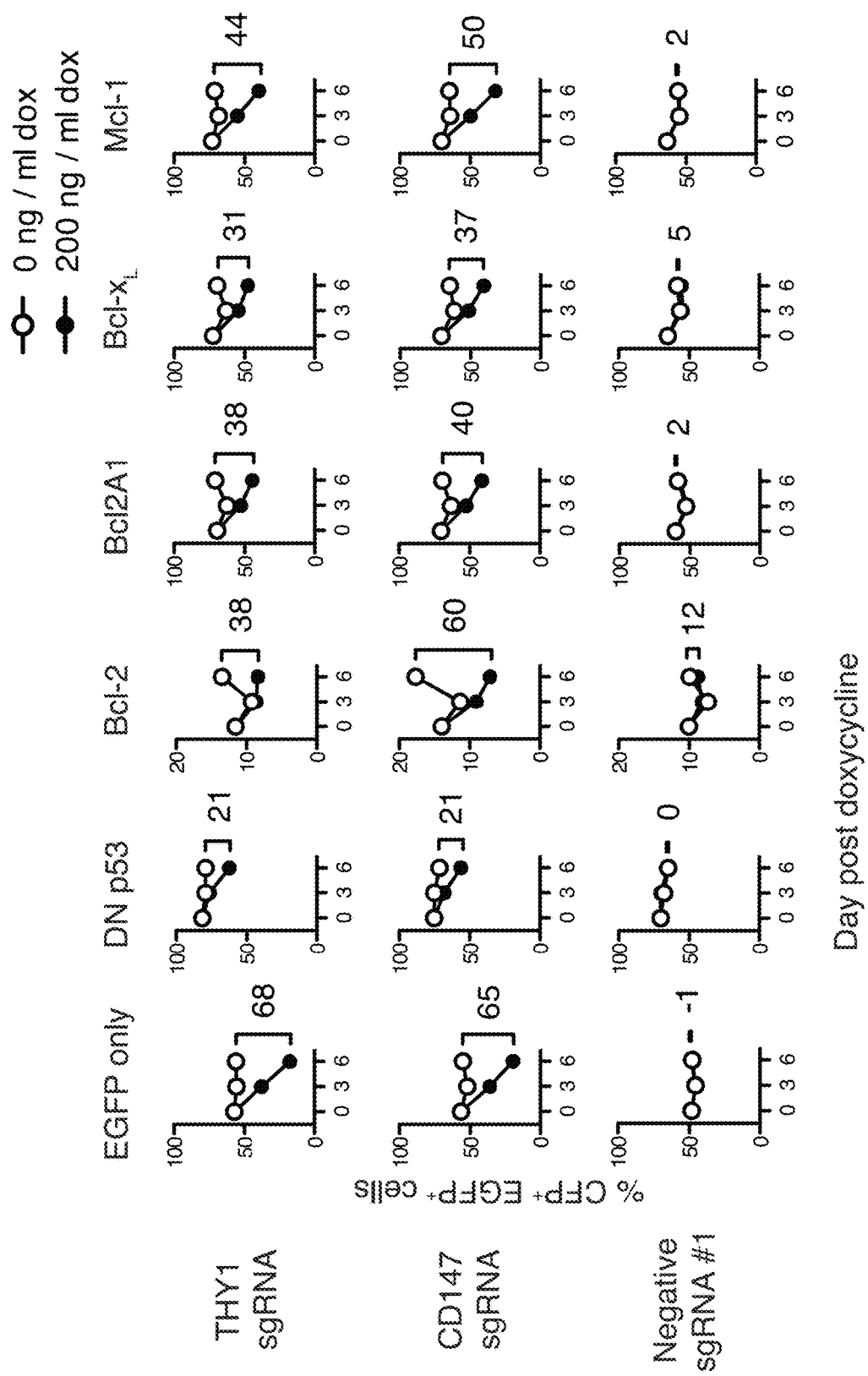
Figure 7:
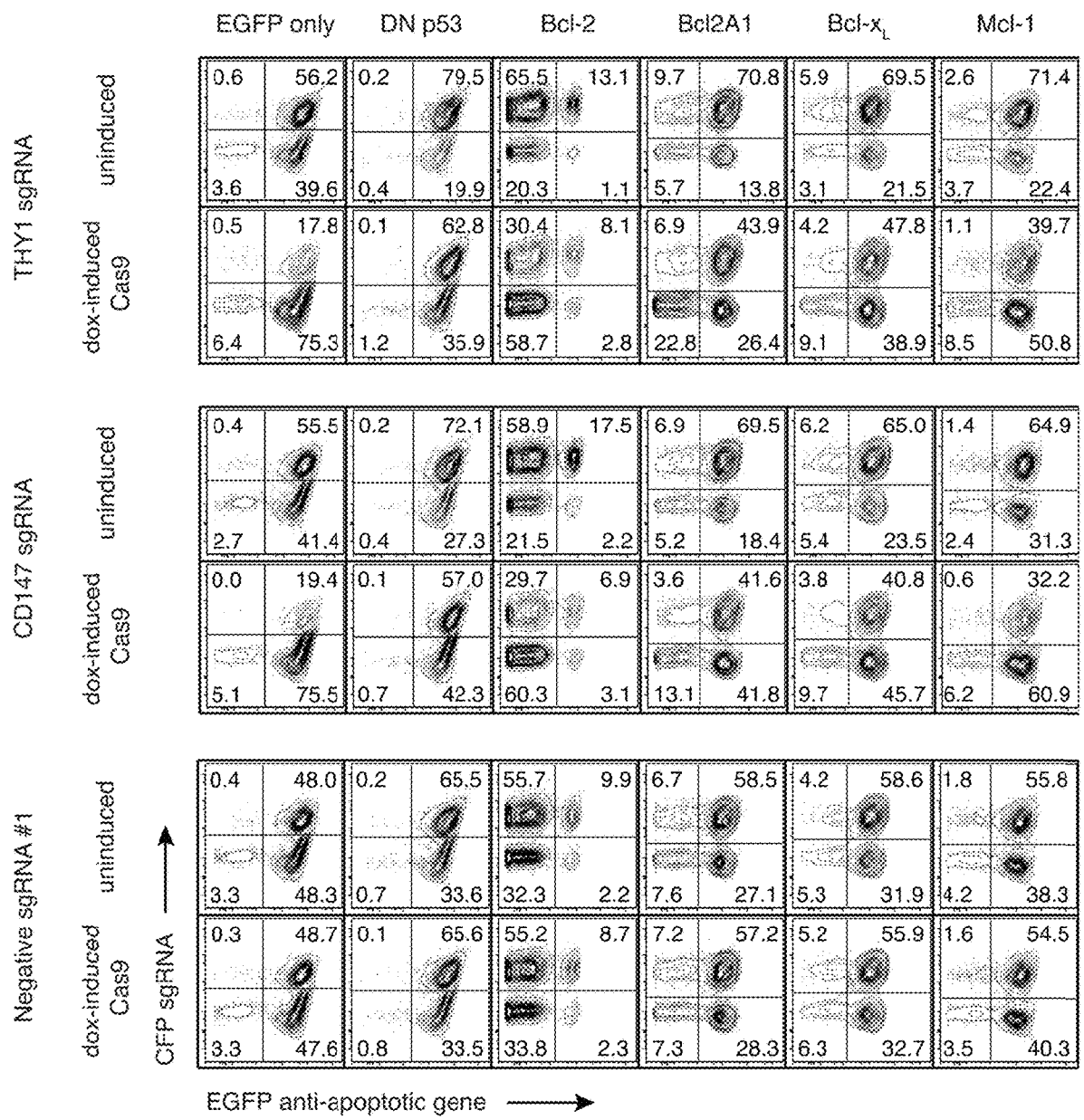
FIG. 7. Flow cytometry plots for the data in FIG. 2 after 6 days with or without doxycycline induction. The percent of CFP$^+$ and/or EGFP$^+$ cells gated on live single cells is shown.
Figure 13A:
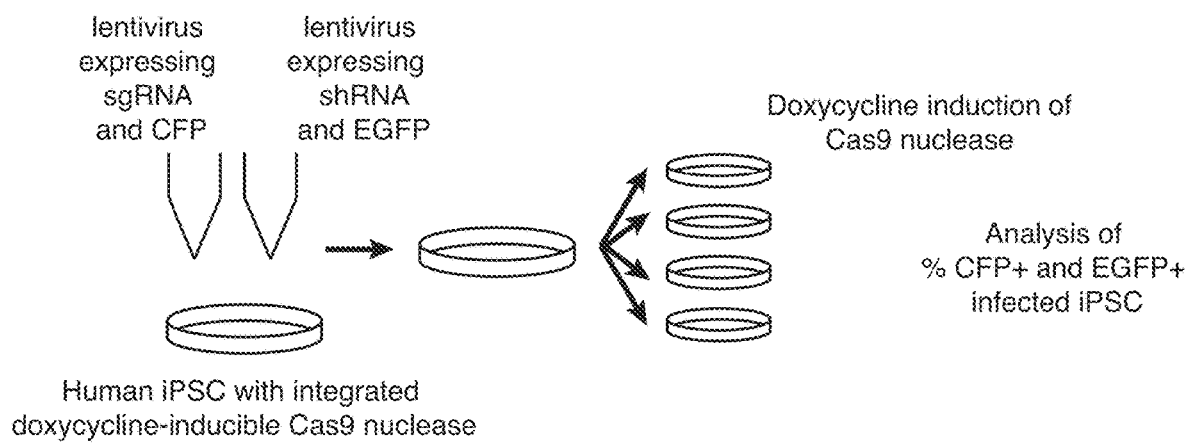
FIG. 13A. Human iPSC containing a doxycycline-inducible Cas9 nuclease were infected with two lentiviruses: one that constitutively expresses CFP along with an sgRNA and another that constitutively expresses EGFP along with an shRNA. One sgRNA targeted the coding region of human THY1; the other was a negative control sgRNA. One shRNA targeted human p53; the other was a negative control shRNA. Three days after infection, each culture was divided into several wells and treated with 0 or 200 ng/ml doxycycline for up to 6 days. At the indicated time points, the percent of CFP$^+$EGFP$^+$ iPSC was determined by flow cytometry.
Figure 13B:
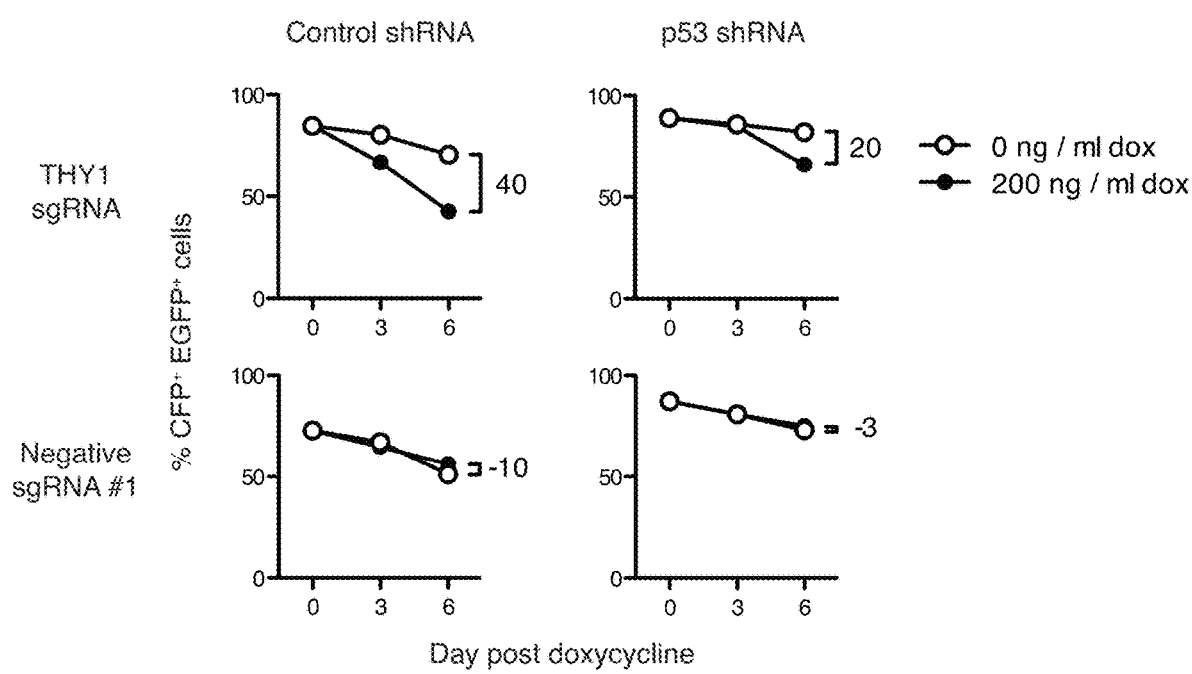
FIG. 13B. The percent of decline of CFP$^+$EGFP$^+$ cells after 6 days of doxycycline induction relative to uninduced cultures is shown.

Next, we sought to rescue the nuclease-mediated death of hiPSC by inhibiting principal apoptotic pathways of the DNA damage response. A second set of lentiviruses was generated to constitutively overexpress EGFP together with an anti-apoptotic gene. To inhibit p53, we overexpressed a dominant negative form of p53 (DN p53) harboring a 288 amino acid deletion known to disrupt p53 tetramerization and enhance hiPSC reprogramming (Hahn et al., 2002; Kawamura et al., 2009). To inhibit the mitochondrial pathway of apoptosis, we overexpressed anti-apoptotic Bcl-2 family members: Bcl-2, Bcl2A1, Bcl-x$_L$, and Mcl-1 (Moldoveanu et al., 2014). The doxycycline-inducible Cas9 hiPSC line was infected with both lentiviruses (6 anti-apoptotic EGFPx3 sgRNA CFP), split into multiple wells, treated with or without doxycycline, and the frequencies of CFP$^+$ and/or EGFP$^+$ cells were assayed at various time points by flow cytometry (FIG. 2 and FIG. 7). With no doxycycline induction of Cas9, the percent of EGFP CFP$^+$ cells remained fairly stable over time, although some anti-apoptotic constructs conferred a growth advantage to the EGFP$^+$ subset. When Cas9 was induced, in the EGFP only negative control construct, the percent of EGFP$^+$CFP$^+$ cells declined by 65-68% (FIG. 2B). The percent of CFP$^+$EGFP$^-$ cells also declined, similar to FIG. 1 (FIG. 7). Each of the anti-apoptotic EGFP lentiviruses was able to abrogate (although not completely eliminate) the EGFP$^+$CFP$^+$ decline compared to the EGFP only control (FIG. 2B). Again, no Cas9 toxicity was seen with the negative control sgRNA. A similar rescue was observed with an shRNA construct to knockdown p53 expression (FIG. 13). Thus, inhibiting p53 or the mitochondrial pathway can partly reduce the nuclease-mediated death in hiPSC.

Example 3

Inhibiting Nuclease-Mediated Death Improves Gene Targeting

Figure 3A:
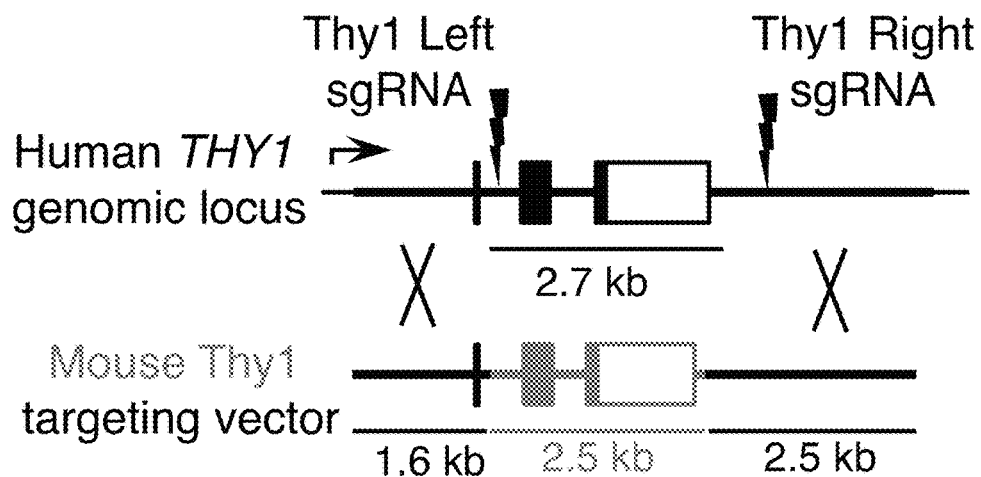
FIGS. 3A-D. Overexpression of anti-apoptotic factors increases gene targeting rates in human iPSC, both for HR-mediated gene replacement and NHEJ-mediated gene excision.

Subsequently, we determined whether rescue by these anti-apoptotic genes would result in higher gene editing frequencies in hiPSC. We used our previously developed and verified model system for assessing targeted gene replacements, where a 2.7 kb segment of the human THY1 gene (hThy1) is replaced with 2.5 kb of its mouse homologue (mThy1) (Byrne et al., 2015) (FIG. 3A). Human Thy1 was chosen because it is expressed on the surface of hiPSC, not essential for cell survival in vitro, and species-specific staining antibodies are available. Two sgRNAs were designed that target hThy1 on either side of the replaced coding region—in intron 1 (Left) or after the polyadenylation sequence (Right). The mThy1 targeting vector plasmid contains the corresponding coding region of mThy1 flanked by hThy1 homology arms outside of the cut sites.

After hiPSC are transfected with the mThy1 targeting vector and plasmids to express the Cas9 nuclease and sgRNAs, the absolute frequencies of gene replacement can be observed using flow cytometry analysis. We have previously shown that, when one sgRNA is used, almost all mThy1$^+$hThy1$^+$ cells have successfully undergone a targeted gene replacement at one allele (heterozygous), and most mThy1$^+$hThy1$^-$ cells have replaced both alleles (homozygous). When both Thy1 sgRNAs are transfected, a fourth population of double negative mThy1$^-$hThy1$^-$ cells also emerges; this largely comprises cells which have excised or inverted the hThy1 alleles, which can also be found in the mThy1$^+$hThy1$^-$ population of these samples (Byrne et al., 2015).

Figure 3B:
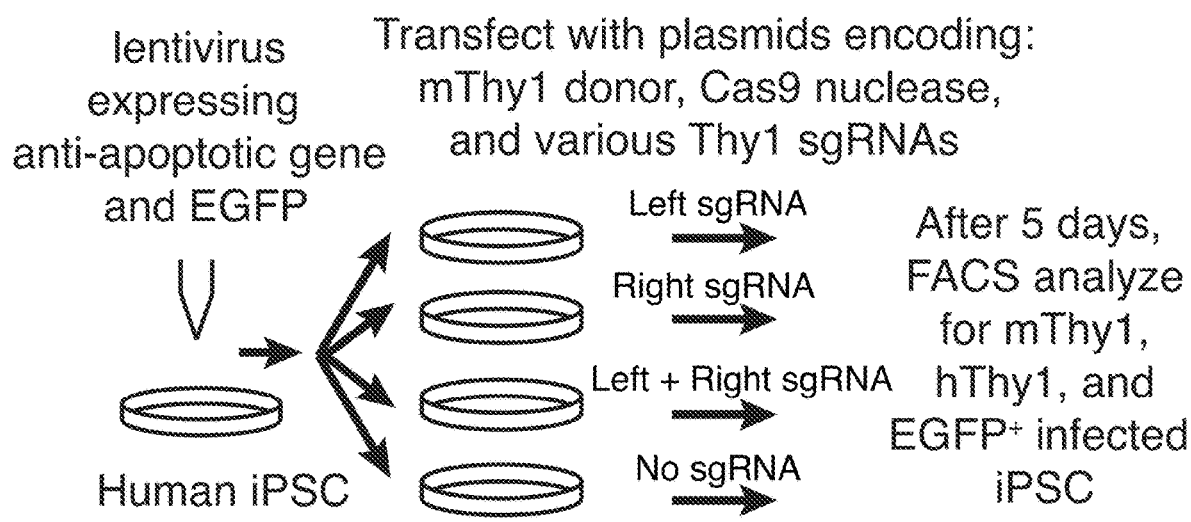
Figure 3C:
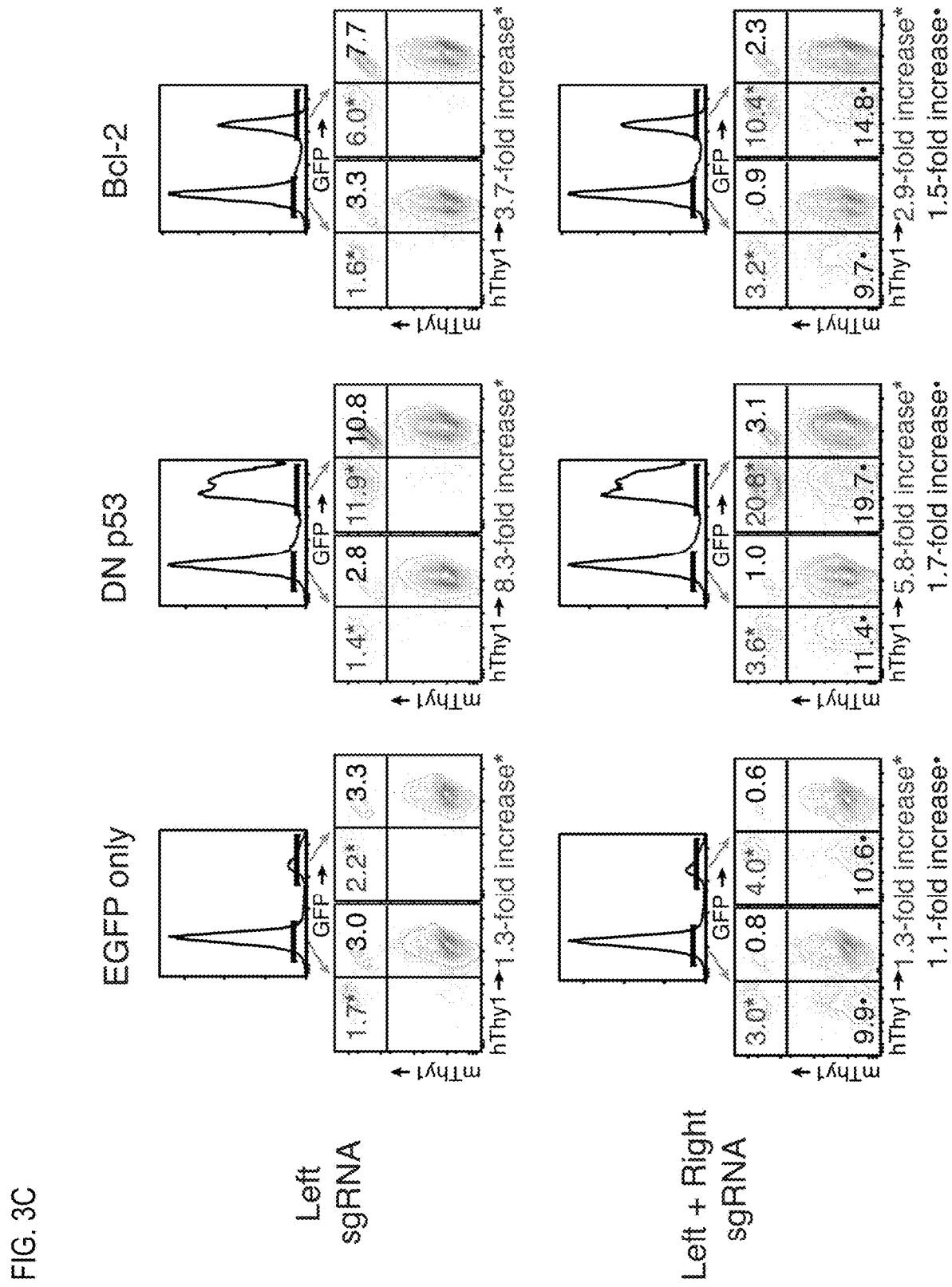
Figure 3D:
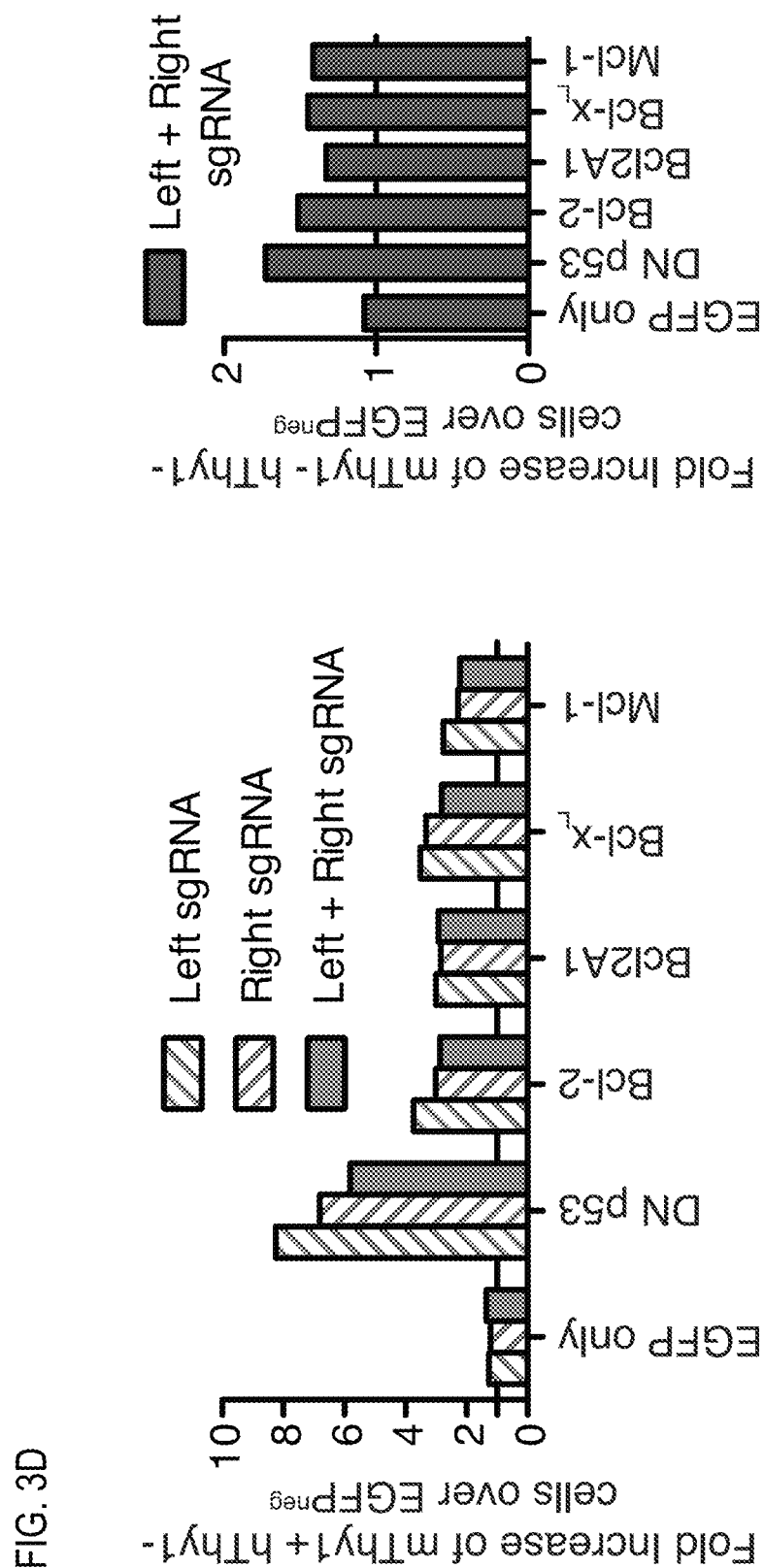

Because our set of anti-apoptotic lentiviral constructs includes an EGFP marker, we could compare gene targeting frequencies between the EGFP$^+$ and EGFP$^-$ subsets within the same transfected cell population. Plain hiPSC were infected with each of the six EGFP anti-apoptotic lentiviruses described in FIG. 2, and then transfected with the mThy1 targeting vector together with plasmids expressing the Cas9 nuclease and either, both, or no Thy1 sgRNAs (FIG. 3B). For the EGFP only control lentivirus, roughly similar gene targeting rates were observed between the EGFP$^-$ and EGFP$^+$ gated subpopulations. Overexpressing DN p53 or Bcl-2 produced a dramatic increase in the frequency of homologous recombination (HR)-mediated mThy1 homozygous gene replacements (FIG. 3C, top row). When both Thy1 sgRNAs were used, overexpressing DN p53 or Bcl-2 also increased the frequency of non-homologous end joining (NHEJ)-mediated hThy1 homozygous gene deletions (FIG. 3C, bottom row). While DN p53 produced the greatest increase in HR-mediated gene targeting (7-8-fold), each of the four Bcl-2 family members also increased gene targeting (3-fold) (FIG. 3D, left). For NHEJ-mediated gene deletions, DN p53 again produced the greatest increase (1.7-fold) versus each of the four Bcl-2 family members (1.3-1.5-fold) (FIG. 3D, right). Gene deletion showed more modest fold increases because the initial frequency was higher. Therefore, rescuing nuclease-mediated death in hiPSC strongly increases the efficiency of both HR-mediated gene replacement and NHEJ-mediated gene deletion.

Example 4

Figure 4A:
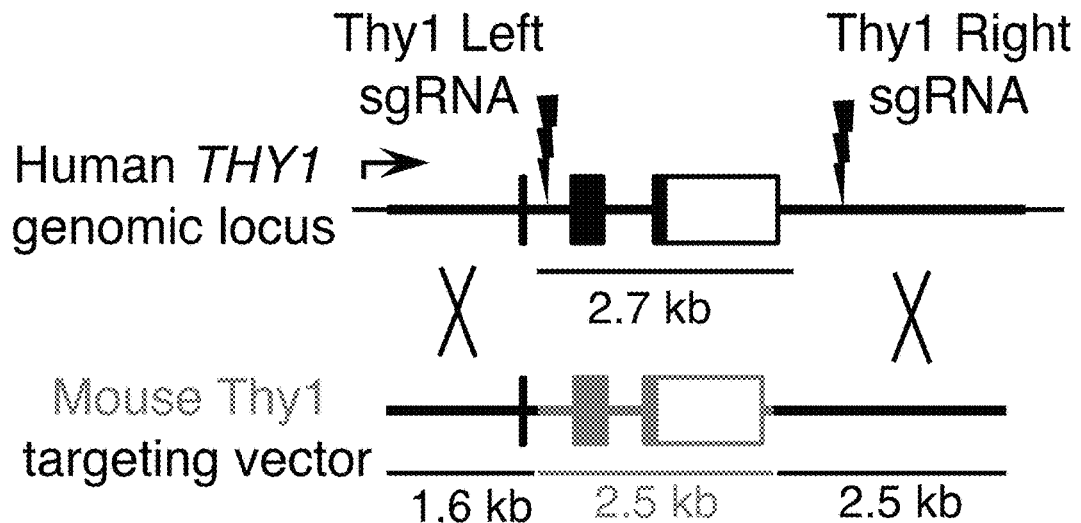
Figure 4B:
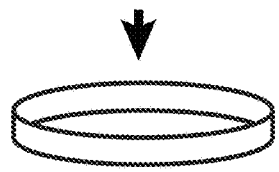

Bcl-2 Improves Gene Targeting when Transiently Transfected with the Cas9 Nuclease Because of their ability to block apoptosis in response to DNA damage, dominant negative forms of p53 and the anti-apoptotic Bcl-2 family members are potent oncogenes, and their permanent overexpression would alter the characteristics of hiPSC and any subsequently differentiated cell types. An ideal anti-apoptotic factor would be capable of rescuing hiPSC and enhancing gene editing when transiently transfected on a plasmid together with the Cas9 nuclease. As the hiPSC culture divides, the cells will lose expression of both the oncogene and the Cas9 nuclease. To test this, we generated a set of plasmids to express the Cas9 nuclease with an anti-apoptotic factor (FIG. 4). Plain hiPSC were transfected with these Cas9 plasmids together with the mThy1 targeting vector and sgRNAs, and gene targeting frequencies were assessed by flow cytometry. Surprisingly, Bcl-2 was the only anti-apoptotic factor that increased gene targeting frequencies compared to Cas9 only controls (FIG. 4C and FIG. 4D). In some cases, the frequency of gene targeting actually declined. While all of the factors increased gene targeting when expressed continuously (FIG. 3), they did not when expression kinetics occurred later. It is unclear why Bcl-2 was uniquely able to improve gene targeting upon transient transfection—each anti-apoptotic gene was artificially overexpressed under the same conditions. However, the different Bcl-2 family members may have qualitative and quantitative differences in their synthesis and affinities of interaction.

Figure 8A:
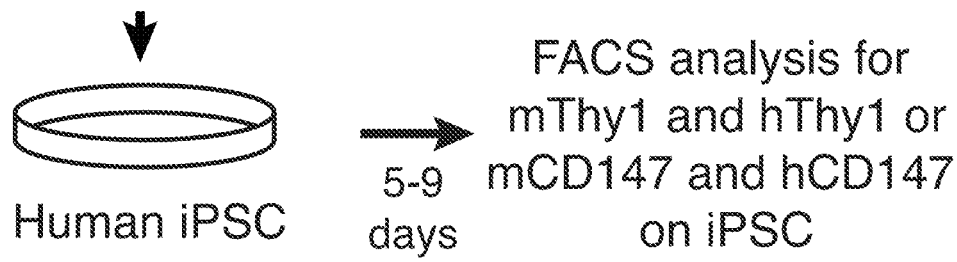
FIGS. 8A-F. Wild type Bcl-2 improves gene targeting at various genomic loci across multiple hiPSC lines.
Figure 8B:
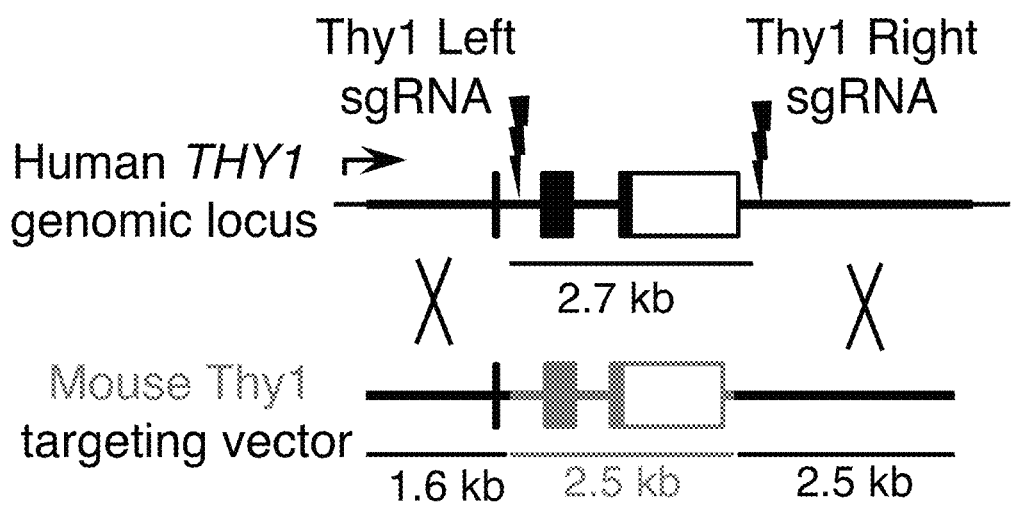
Figure 8C:
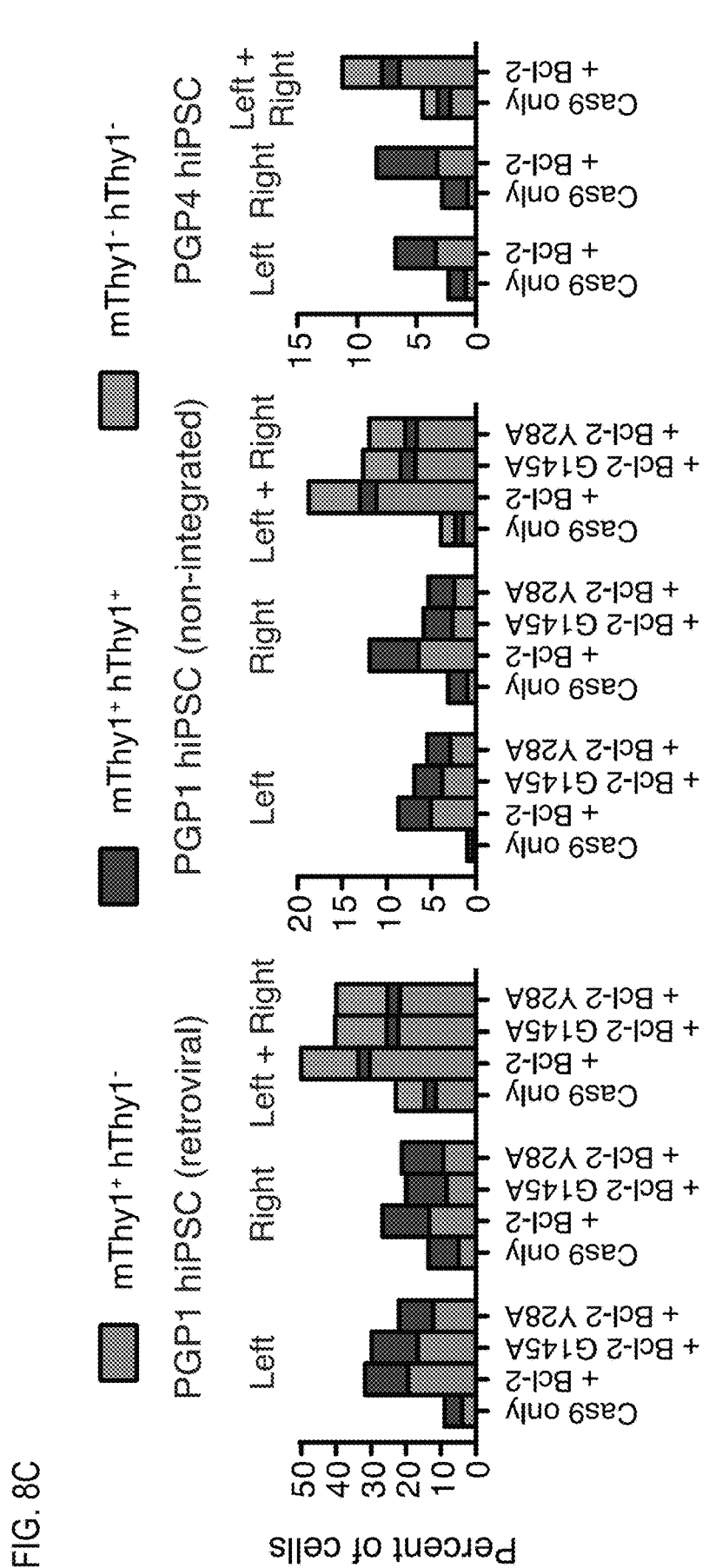

To further investigate the mechanism by which Bcl-2 was able to improve gene targeting, we tested previously characterized mutant forms of Bcl-2. The G145A mutation in the BH1 domain prevents Bcl-2 from interacting with Bax and inhibiting apoptosis. Alternatively, the Y28A mutation in the BH4 domain does not block Bax interaction, but may be required for Bcl-2 inhibition of the cell cycle (Huang et al., 1997; Youn et al., 2004), although there are conflicting reports (Janumyan et al., 2003). For enhanced transfection efficiency, the sgRNA segment was cloned onto the Cas9 nuclease expression plasmid ("Cas9 only sgRNA" or "Cas9 Bcl-2 sgRNA"). This set of plasmids, together with the mThy1 targeting vector, was transfected into plain hiPSC, and gene targeting frequencies were assessed using flow cytometry (FIG. 8). Surprisingly, both mutations showed intermediate levels of gene targeting compared to wild type Bcl-2, which showed the greatest enhancement. Bcl-2's protective effects were more pronounced on a different hiPSC line, reprogrammed through non-integrating methods, although the absolute mThy1 targeting frequencies were lower (FIG. 8C). Even if the Y28 mutation does not affect the anti-apoptotic function of Bcl-2, its N-terminal BH4 domain may still be involved, as truncation mutants or caspase cleavage of this domain can prevent anti-apoptotic activity (Cheng et al., 1997).

Figure 9A:
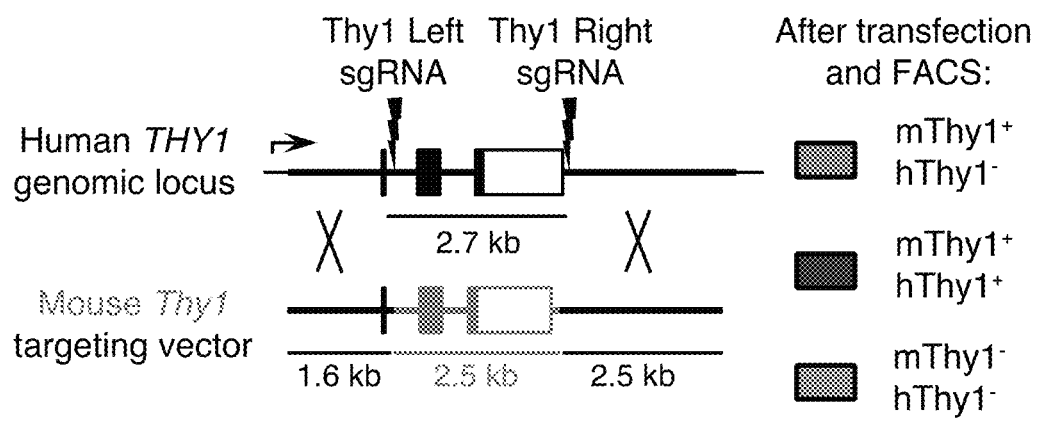
FIGS. 9A-G. Effects of chemical and genetic inhibitors on mThy1 gene targeting in hiPSC.
Figure 9B:
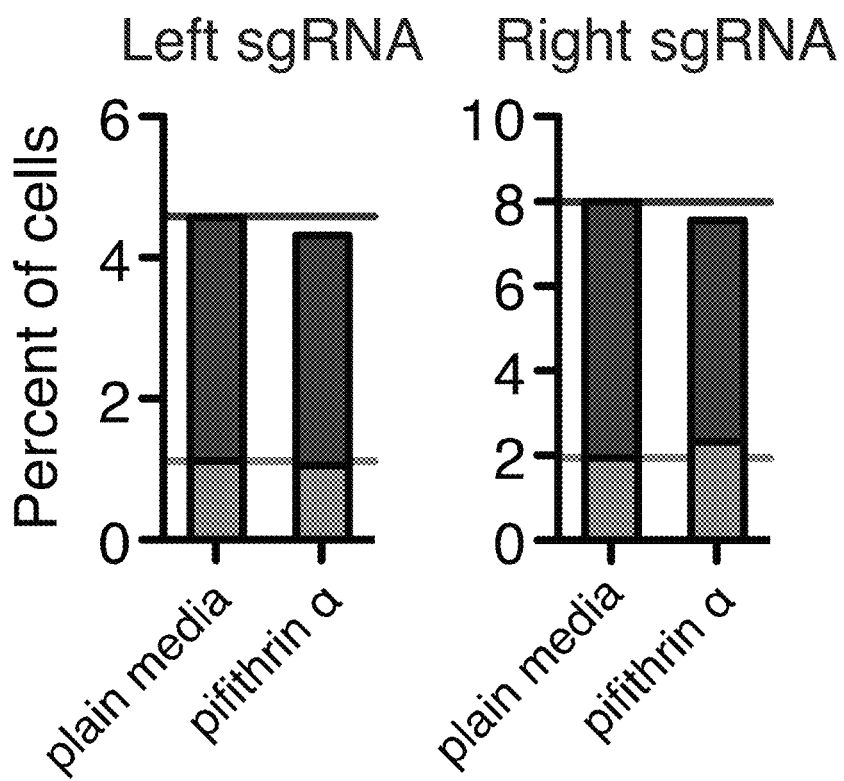
Figure 9C:
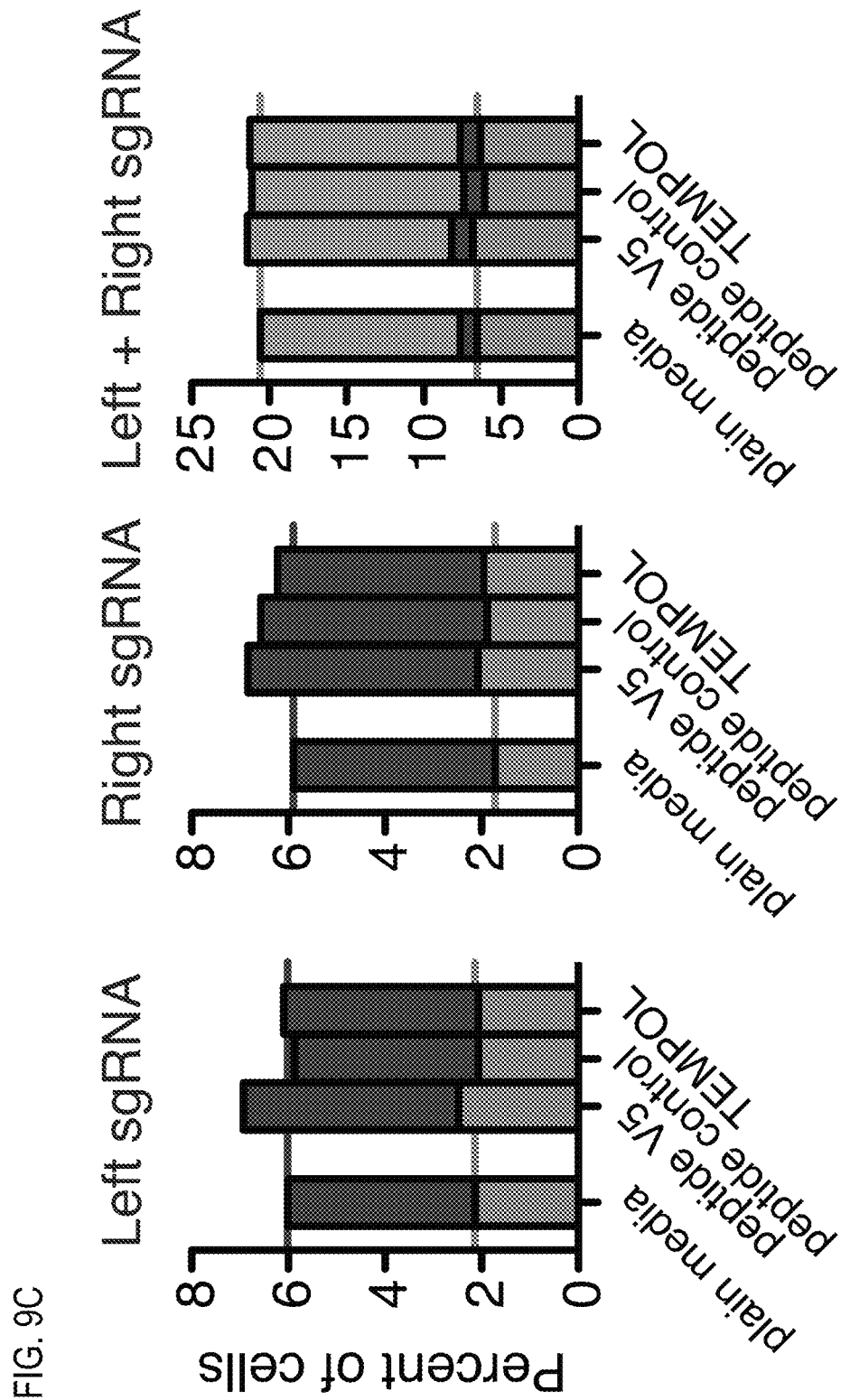

Next, we tested several chemical inhibitors of p53 and Bax. None of these inhibitors promoted mThy1 gene targeting in hiPSC when applied after transfection. Pifithrin α, which blocks p53-dependent transcriptional activation, has been shown to rescue mouse, but not human, ES cells from UV-induced apoptosis (Grandela et al., 2007; Qin et al., 2007), but did not enhance hiPSC gene targeting (FIG. 9A, FIG. 9B). Pifithrin μ does not affect p53 transcriptional activation, but does prevent p53 from binding to Bcl-2 and Bcl-$x_L$ at the mitochondria and has been shown to improve hESC survival after genotoxic stressors (Garcia et al., 2014; Grandela et al., 2007; Qin et al., 2007). However, it exhibited considerable toxicity to hiPSC when applied for 2 days after nucleofection (10-20 μM, data not shown) instead of a few hours as used in previous studies. The Bax inhibiting pentapeptide V5 (VPMLK, SEQ ID NO:31), derived from the human Ku70 Bax-binding domain (Yoshida et al., 2004), produced only a very slight improvement in gene targeting (FIG. 9C). These Ku-derived peptides may not be effective on the active conformation of Bax maintained in hiPSC. The mitochondrial apoptosis-induced channel blockers iMAC1 and iMAC2 (Peixoto et al., 2009) were toxic to hiPSC at 2.5-10 μM. The antioxidants N-acetyl cysteine (1-5 mM) or TEMPOL showed toxicity or no effect, respectively (FIG. 9C).

Example 5

Figure 10A:
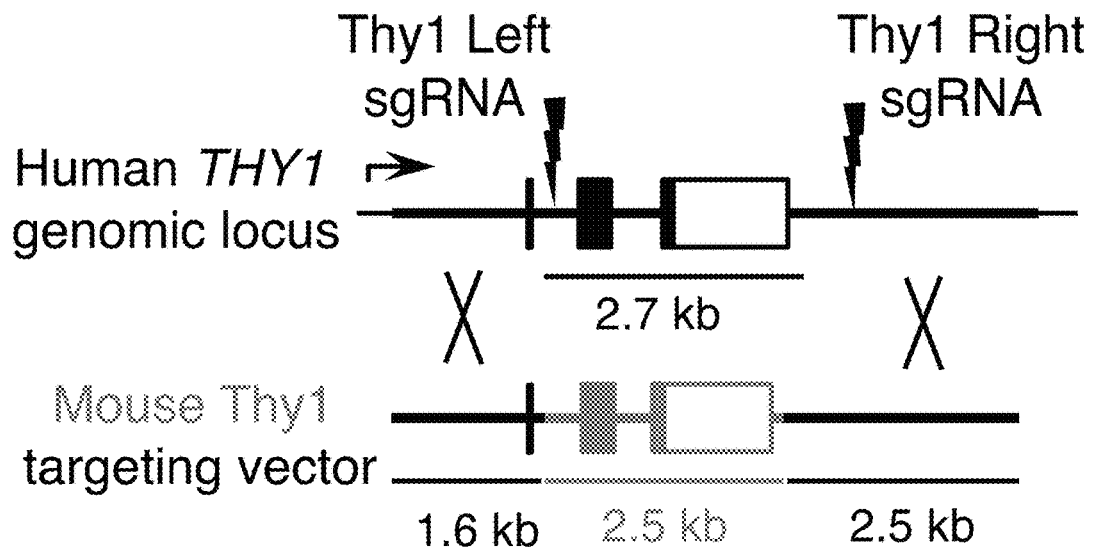
FIGS. 10A-F. Effect of Caspase and p38 MAPK inhibitors on survival and gene targeting of human iPSC.
Figure 10B:
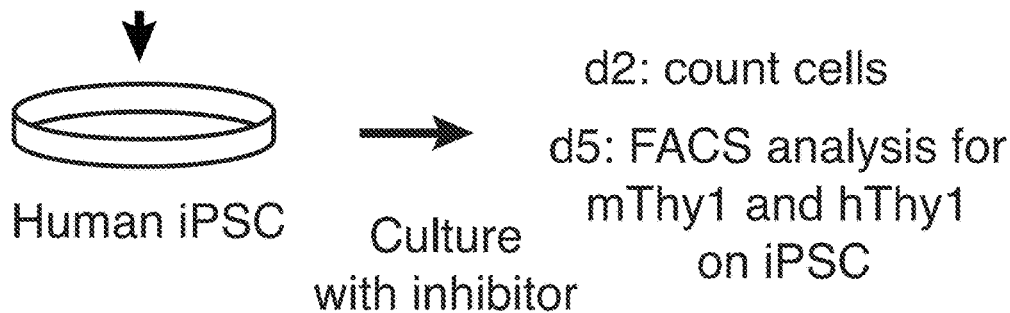
Figure 10C:
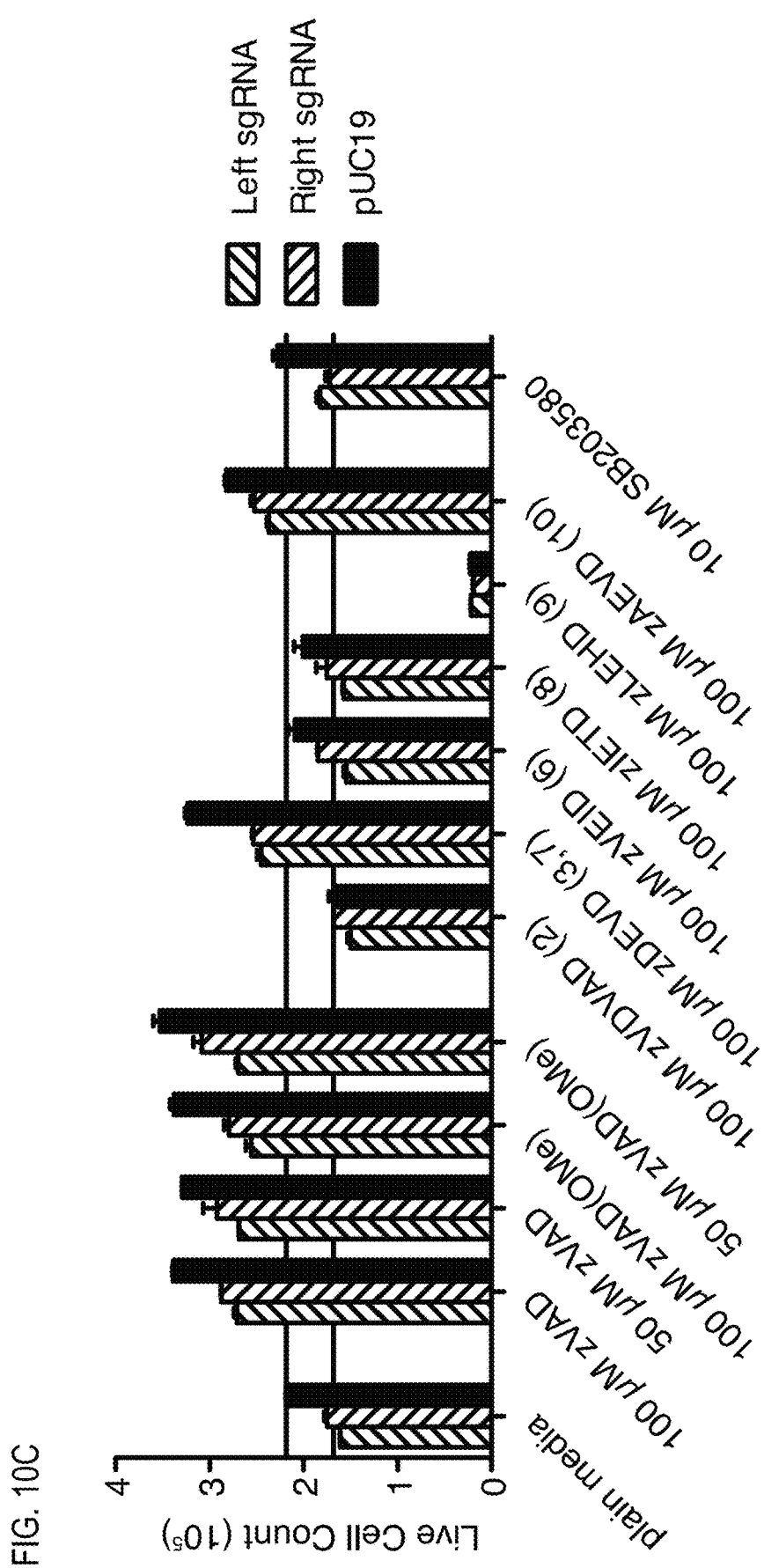
Figure 10D:
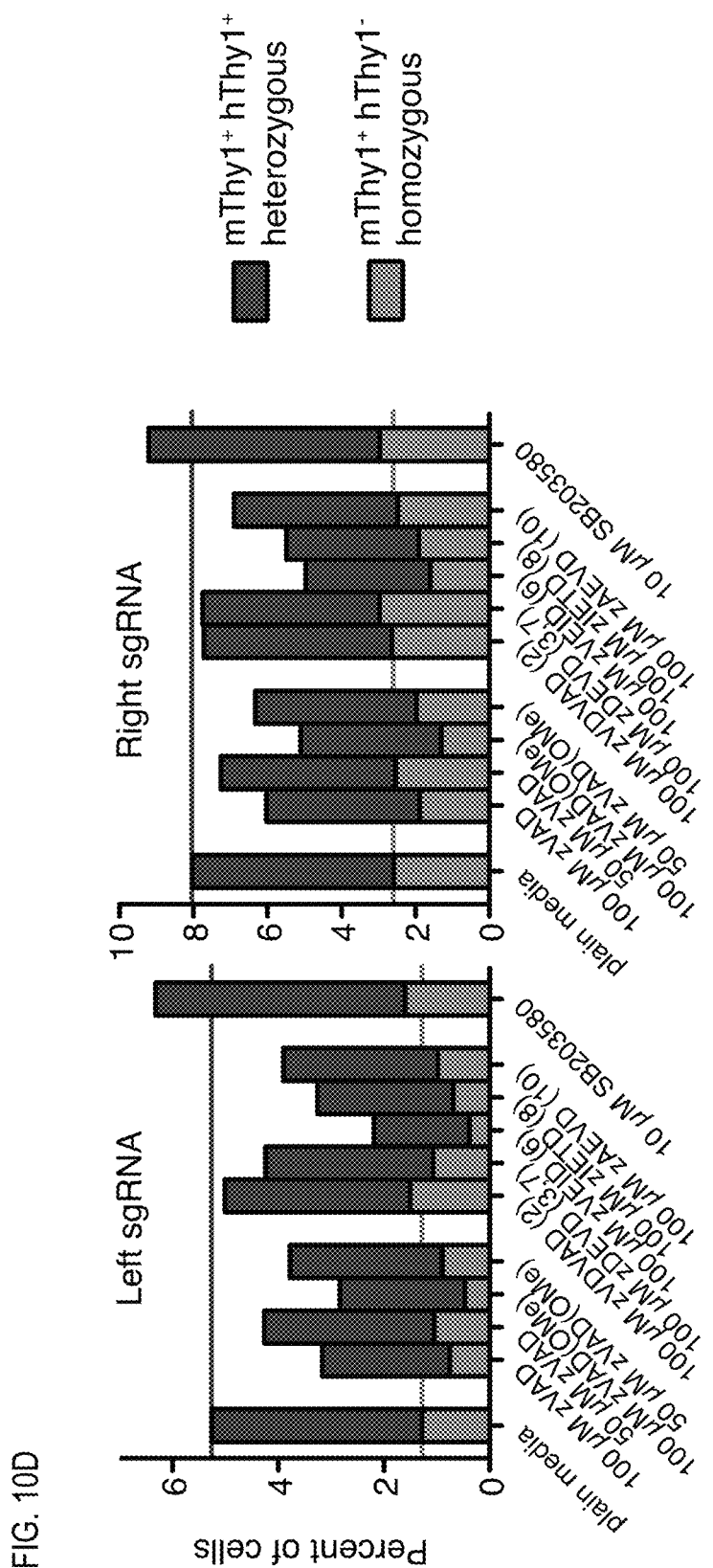
Figures 10E, 10F:
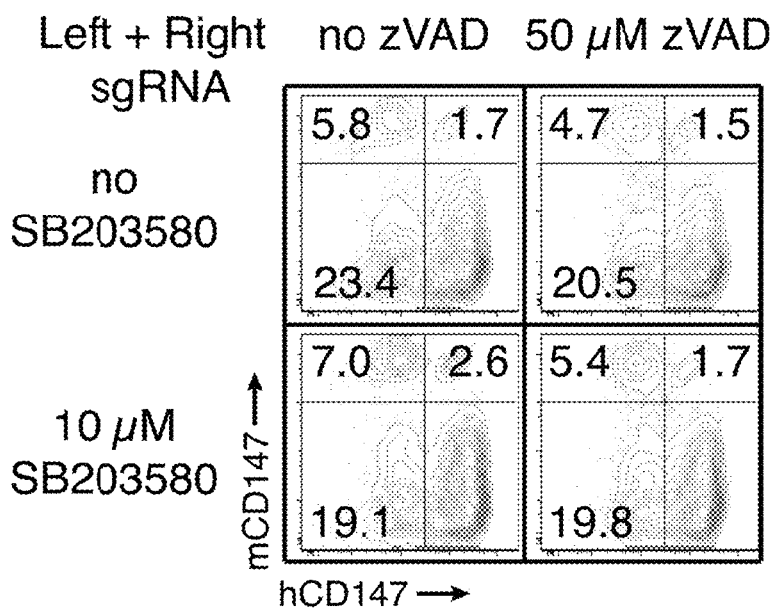
Figure 11A:
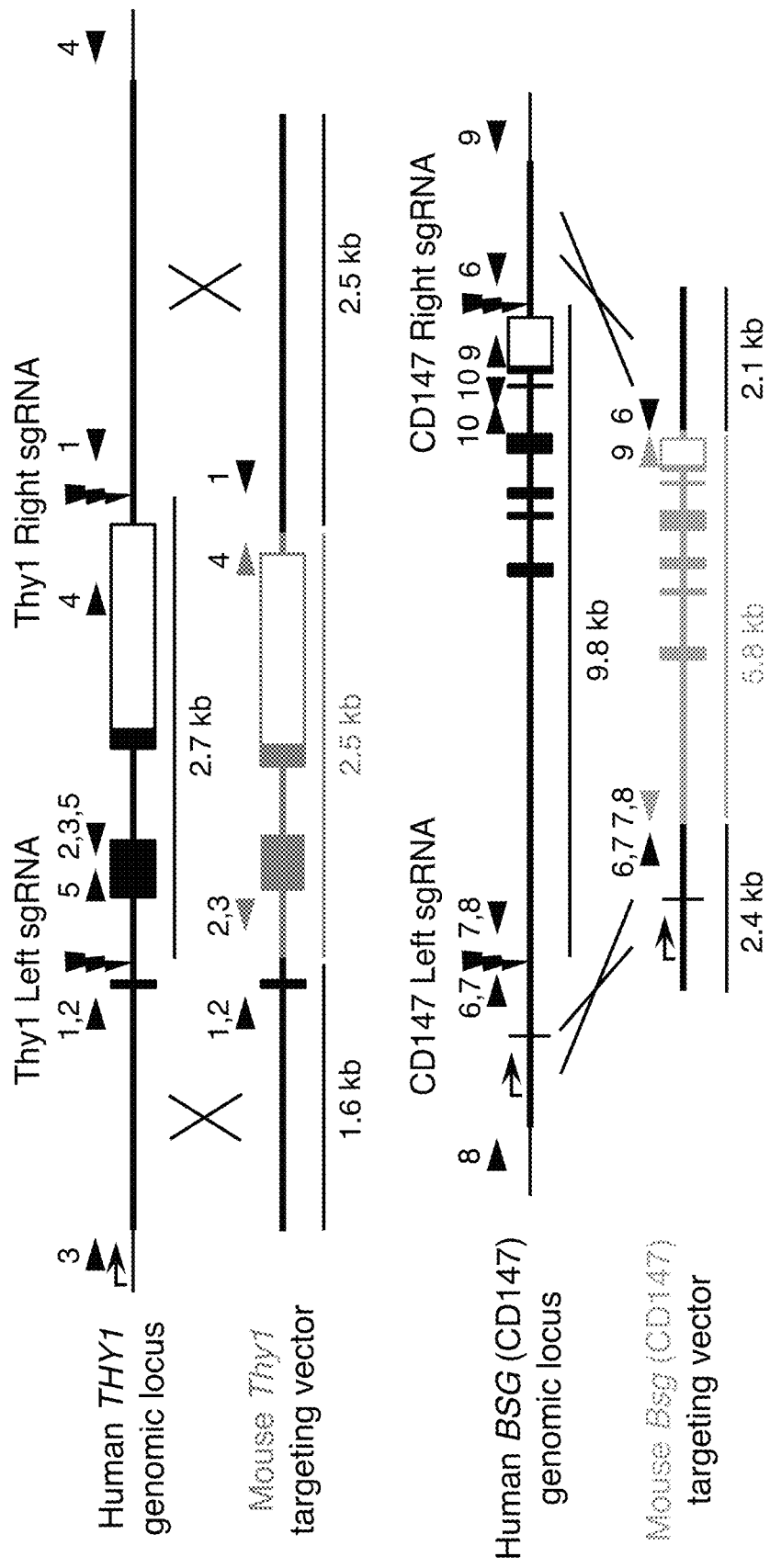

Caspase Inhibitors Rescue hiPSC Death from Dissociation but not Nuclease Activity We then tested chemical caspase inhibitors after hiPSC transfection. As seen in previous studies, more cell death was observed when a sgRNA-expressing plasmid was transfected compared to an equivalent amount of pUC19 empty vector (Byrne et al., 2015) (FIG. 10). The pan-caspase inhibitors zVAD-fmk and zVAD(OMe)-fmk rescued cells transfected with an sgRNA, and also those transfected with the pUC19 control. Despite this overall rescue, the difference between the sgRNA and pUC19 cell counts remained about the same (FIG. 10C). Caspase inhibitors have been shown to prevent detachment-mediated cell death (anoikis) of human ES cells (Wang et al., 2009), which would explain why inhibiting caspases improves the survival of all hiPSC following nucleofection. Caspase inhibitors also increased hiPSC recovery following single cell FACS sorting (in conjunction with SMC4 inhibitors) (FIG. 10F). However, rescuing hiPSC with pan-caspase inhibitors actually decreased the gene targeting frequencies compared to plain media, which could be due to inhibition of the cell cycle (FIGS. 10D, 10E). Adding zVAD did not affect the doxycycline-induced Cas9 nuclease toxicity shown in FIG. 1.

More specific caspase inhibitors (zDEVD-fmk and zAEVD-fmk) also prevented anoikis (FIG. 10C). zDEVD preferentially inhibits the executioner caspases 3 and 7. zAEVD is often sold as a specific inhibitor of caspase 10, which cleaves and activates caspases 3 and 7 downstream of surface death receptor signals, but zAEVD can inhibit other caspases as well (Garcia-Calvo et al., 1998). Surprisingly, the caspase 9 inhibitor zLEHD-fmk was very toxic to hiPSC; however, it can also inhibit caspases 3, 6, and 8, and may be more potent than zVAD (Berger et al., 2006; McStay and Green, 2014). Lower concentrations (25 μM) did not show as much anoikis rescue (zVAD or zDEVD) or toxicity (zLEHD).

The p38 MAP kinase inhibitor SB203580 was reported to enhance HR in response to a dsDNA break (Golding et al., 2007) and is also included in some protocols for deriving naive human pluripotent stem cells (Gafni et al., 2013). Adding 10 μM SB203580 to the hiPSC media after nucleofection did not affect cell survival, but did enhance gene targeting efficiency (FIGS. 10C-E). Future experiments included 50 μM zVAD and 10 μM SB203580 after hiPSC transfection as it produced the best balance regarding anoikis rescue, gene targeting efficiency, and price.

Example 6

Simultaneous Multiplex Large Gene Replacements

Figure 5A:
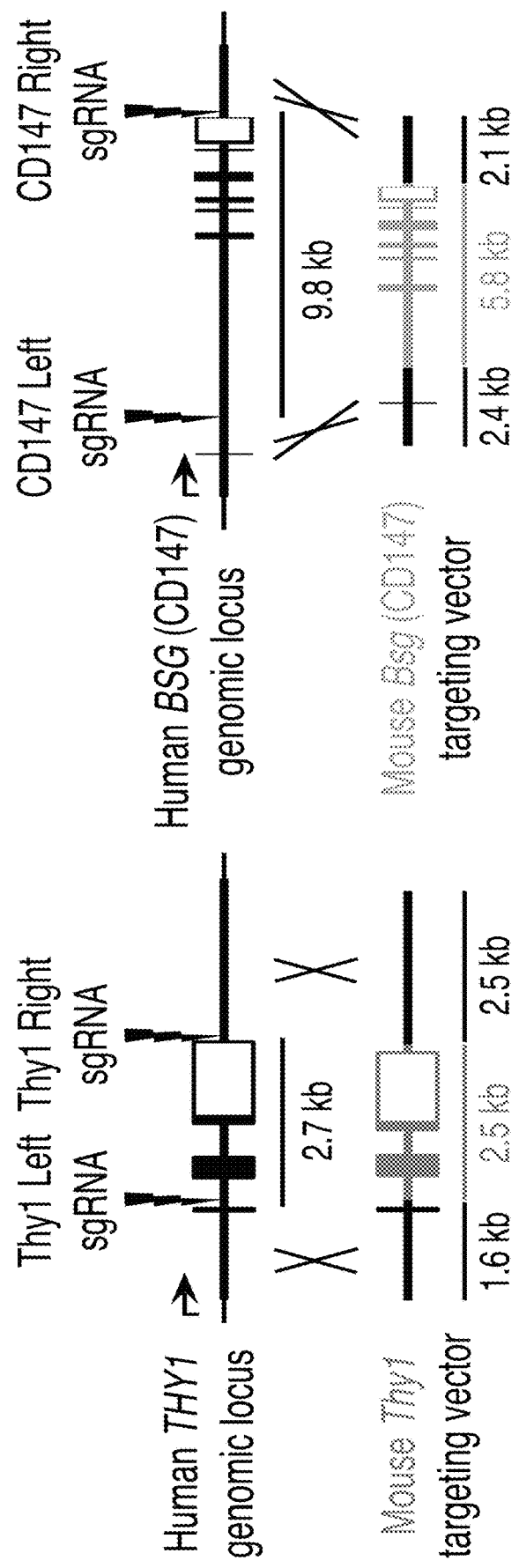
Figure 8D:
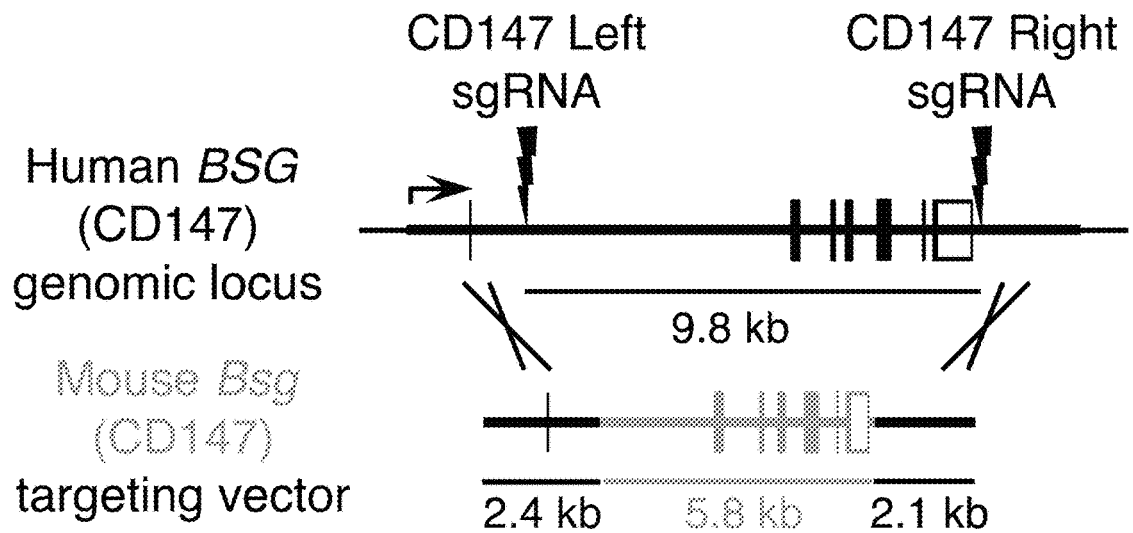
Figure 8E:
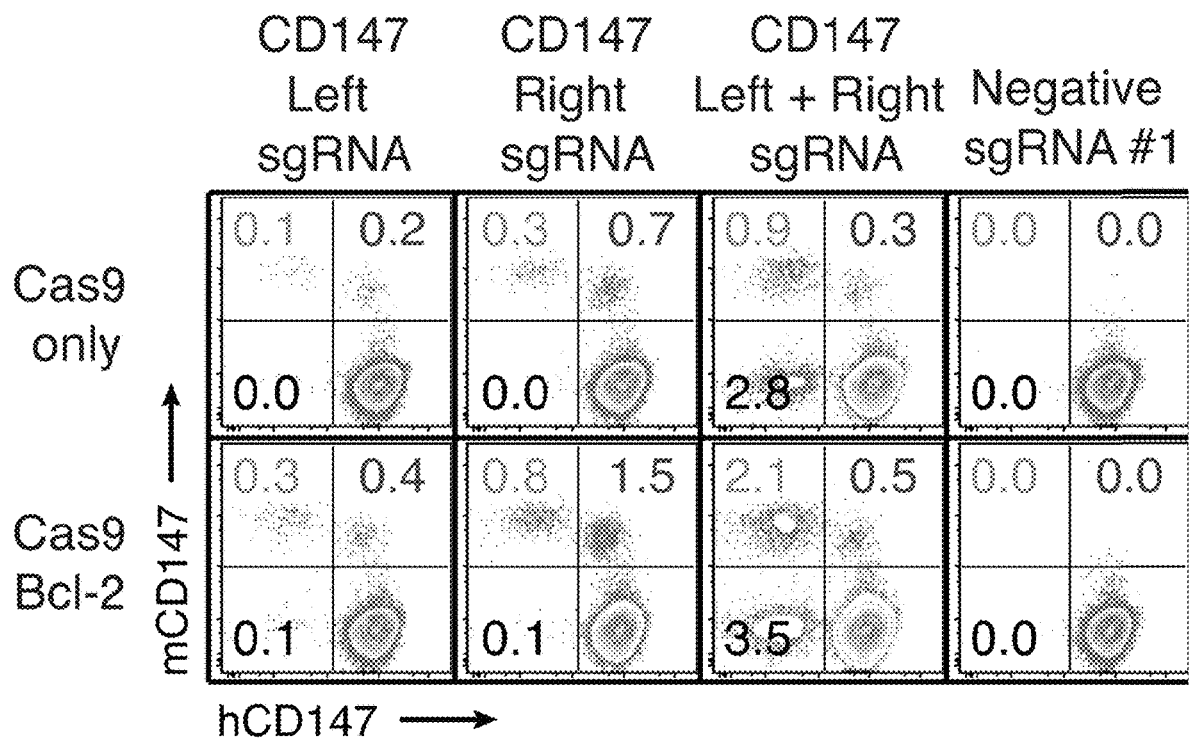
Figure 8F:
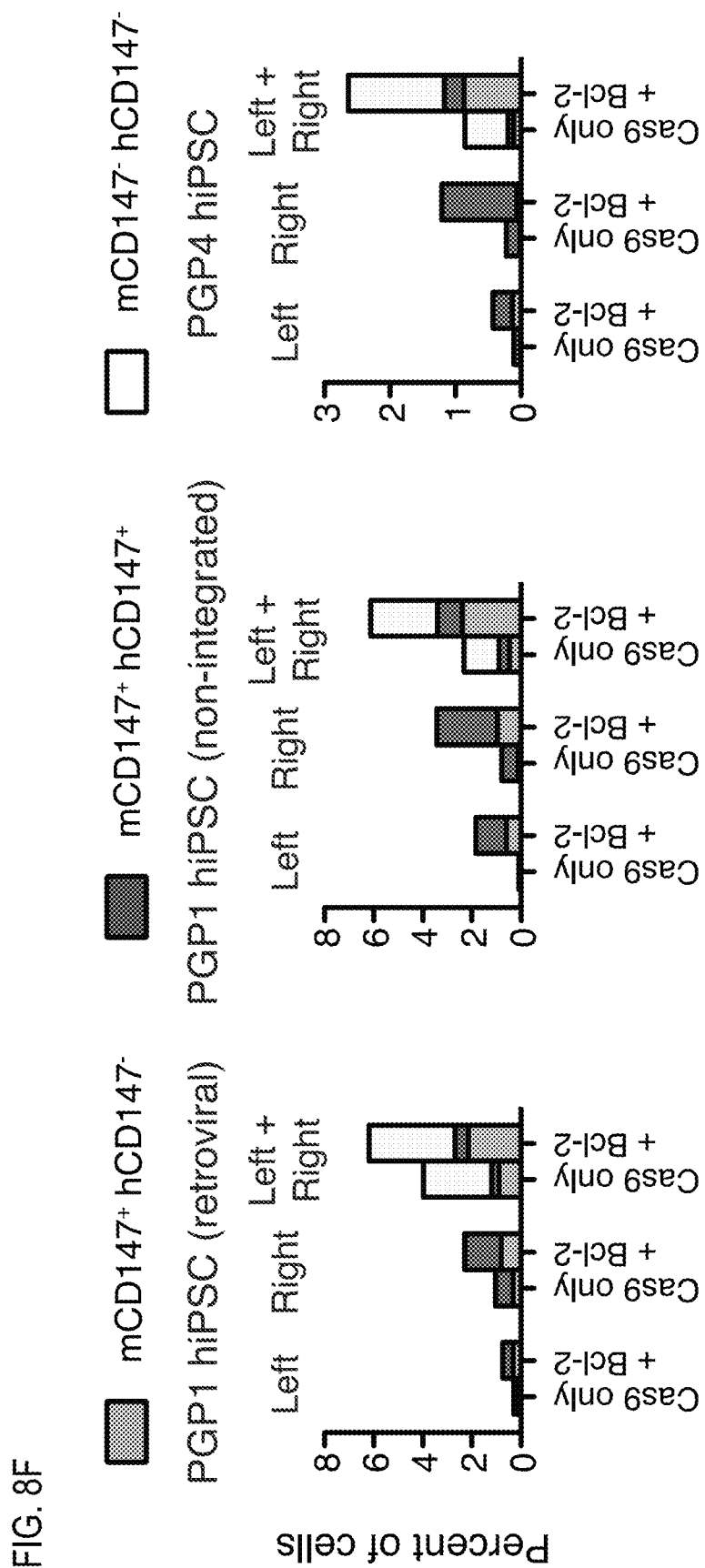

We confirmed Bcl-2's ability to improve gene targeting at a second gene locus using our previously published similar scheme for human Basigin (BSG, CD147) (Byrne et al., 2015). Like hThy1, CD147 is expressed on the surface of hiPSC, not essential for hiPSC survival in vitro, and good staining antibodies are available. Similar to the mThy1 targeting scheme, two sgRNAs, 9.8 kb apart, target human BSG either in intron 1 or after the polyadenylation sequence. The mouse CD147 targeting vector plasmid encodes 5.8 kb of the corresponding mouse CD147 coding region flanked by homology arms outside of the cut sites (FIG. 5A and FIG. 8D). We have previously demonstrated that, after transfection, a similar pattern of multi-kilobase homozygous and heterozygous gene replacement for mCD147 can be observed using flow cytometry, including excision and inversion alleles when both CD147 sgRNAs are used (although the larger CD147 gene replacements occurred less frequently) (Byrne et al., 2015). Including Bcl-2 on the Cas9 plasmid substantially and reproducibly increased gene targeting frequencies, in both retroviral and non-integrating PGP1 hiPSC lines (FIGS. 8E-F). A third hiPSC line, which was retrovirally-reprogrammed from a different donor (PGP4), also showed markedly improved gene targeting with Bcl-2 at the CD147 and Thy1 loci (FIGS. 8C, 8F).

Figure 12:
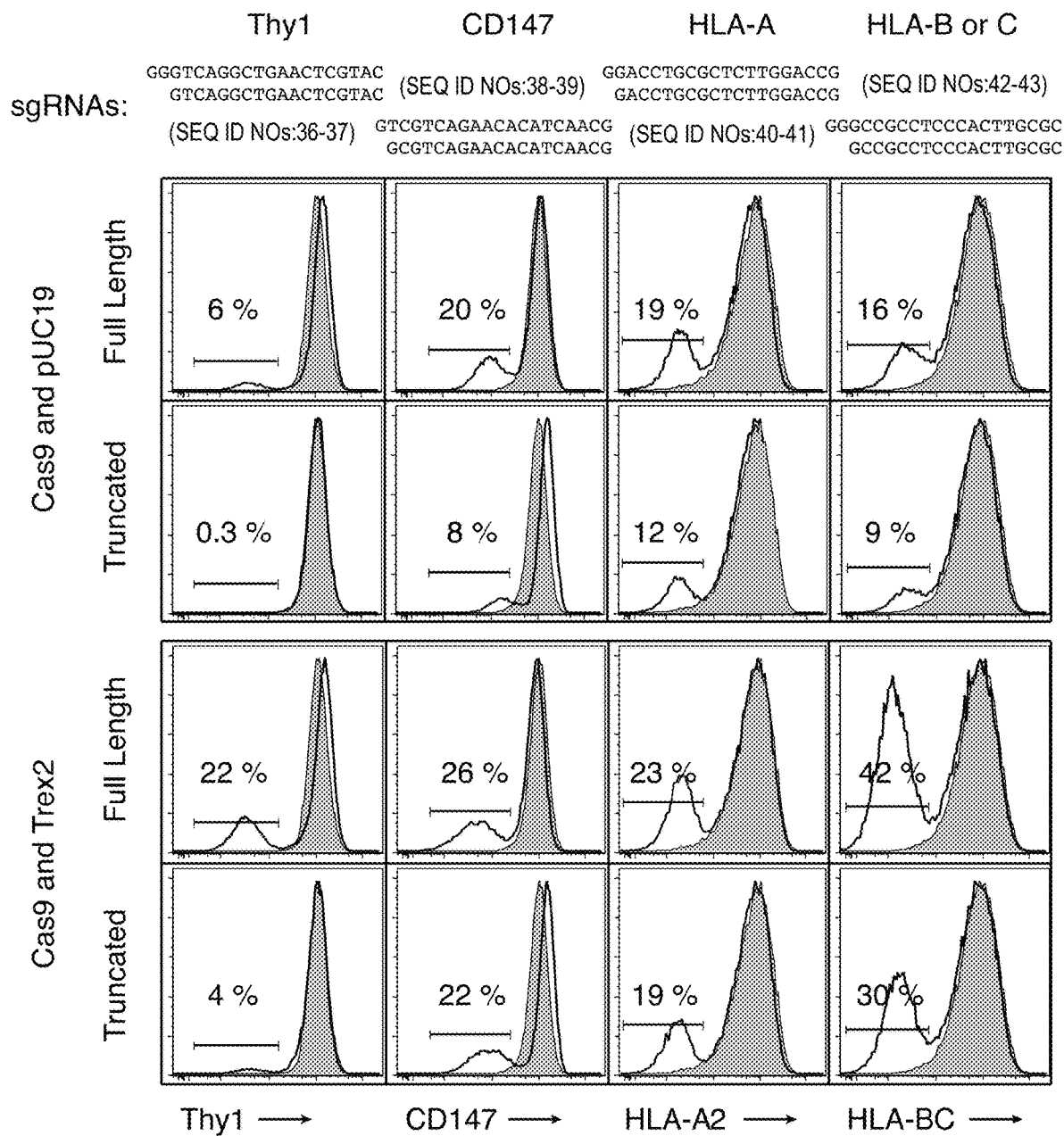
FIG. 12. Gene disruption activity of truncated sgRNAs with and without the Trex2 endonuclease. Full length (20 bp of target complementarity) and Truncated (18-19 bp) sgRNAs were designed to target the coding region of four genes expressed on the surface of hiPSC (top) and cloned into expression plasmids under the constitutive U6 promoter. The Cas9 nuclease and Trex2 endonuclease were also cloned into separate expression plasmids under the constitutive EF1α promoter. Human iPSC were nucleofected with 0.5 µg Cas9 plasmid, 1 µg sgRNA plasmid, and 1 µg of either pUC19 control or Trex2 plasmid. Five days later, cells were stained for expression of the surface markers (Thy 1, CD147, HLA-A2, or HLA-BC) and analyzed by flow cytometry gated on live single cells (open histograms). Shaded histograms indicate staining of an untargeted hiPSC control. The percent of cells that have lost expression of the surface markers is shown.

Previously, low gene targeting frequencies in hiPSC could be overcome by clever enrichment or selection schemes. However, for simultaneous multiplex gene targeting, a higher absolute frequency is needed. To demonstrate the ability of transient Bcl-2 overexpression to achieve multiplex large gene replacements, we combined our mThy1 and mCD147 gene targeting systems (FIG. 5). Plain hiPSC were transfected with both mThy1 and mCD147 targeting vectors together with the "Cas9 only sgRNA" or "Cas9 Bcl-2 sgRNA" plasmids. Combinations of both Left sgRNAs, both Right sgRNAs, all four sgRNAs, or a negative control sgRNA were used. Cultures were then analyzed by flow cytometry for hThy1, mThy1, hCD147, and mCD147 expression. In each case, samples transfected with only the Left or only the Right sgRNAs showed the expected patterns of homozygous and heterozygous gene replacement for each locus, whereas only the samples transfected with all four sgRNAs showed substantial double-negative (or quadruple-negative) populations (FIG. 5B). In every instance, inclusion of Bcl-2 improved gene editing frequencies. When cell populations were gated on homozygous mThy1 gene replacement (red) and then analyzed for mCD147 gene replacement, we found an enrichment of mCD147 events, rather than an independent assortment of gene editing outcomes. Likewise, when all four sgRNAs were transfected, the mThy1$^-$hThy1$^-$ double negative population (blue) contained an enriched proportion of mCD147$^-$hCD147$^-$ cells. Even considering an overall transfection rate of 60-70%, these enrichments indicate that hiPSC may be poised for either HR or NHEJ at various periods. With Bcl-2, the frequency of HR-mediated double homozygous gene replacements (mThy1$^+$hThy1$^-$ mCD147$^+$hCD147$^-$) increased by an order of magnitude (Left sgRNAs: from 0.02% to 0.16%; Right sgRNAs: from 0.01% to 0.37%). NHEJ-mediated quadruple-negative deletions (mThy1$^-$ hThy1$^-$ mCD147$^-$hCD147$^-$) increased from 0.7% to 1.1% (FIG. 5B). Quadruple-targeted hiPSC were cloned using single cell FACS sorting and expanded. Their genotypes were confirmed using ten PCR reactions; they retained expression of pluripotent markers; and they possessed normal karyotypes (FIG. 12).

Example 7

Engineering Single Base Pair Changes with High HR Frequency

Figure 6A:
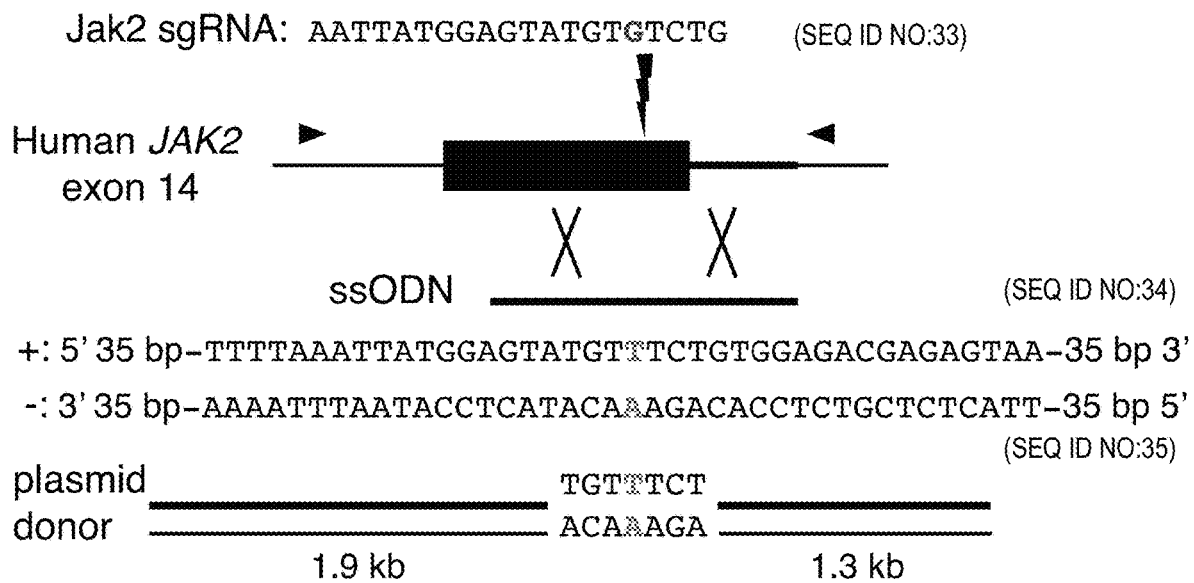
Figure 6B:
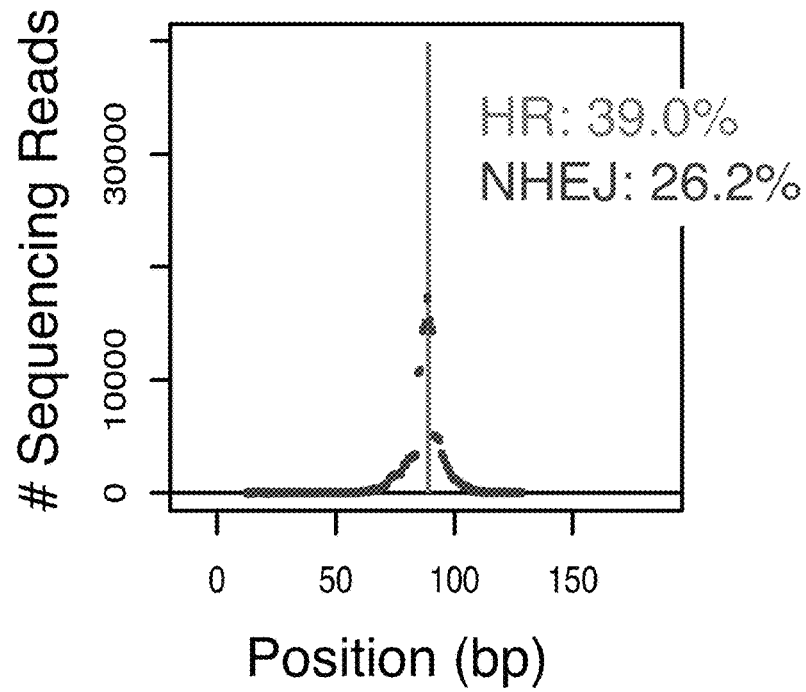

While multi-kilobase mouse gene replacement is a valuable model system for readily assessing gene editing outcomes, many hiPSC experiments aim to study small disease variants. For engineering particular point mutations, single-stranded oligodeoxynucleotide (ssODN) donors are often preferred instead of plasmids. To demonstrate the use of Bcl-2 overexpression to engineer a disease mutation in hiPSC, we chose the Jak2 V617F mutation, which is the most commonly affected gene in myeloproliferative neoplasms (MPN). This mutation generates disease outcomes of varying severity, but studies have been complicated by differences in patient's genetic backgrounds, so an isogenic model system is desired (Chen et al., 2010). Human iPSC were transfected with the aforementioned Cas9-Bcl-2 plasmid constructs containing an sgRNA targeting Jak2 (Smith et al., 2014) together with 110 bp ssODN donors (in either orientation) or a plasmid donor (FIG. 6A). Gene editing rates were measured using PCR and next-generation sequencing around the cut site to examine both incorporation of the mutation (HR) and indels (NHEJ) (FIG. 6B) (Guell et al., 2014). Including Bcl-2 on the Cas9 plasmid substantially increased the absolute recombination frequencies—with oligo donors it increased by 2-4-fold, whereas with plasmid donors it increased from 25% to 39% (FIG. 6C). Donor ssODN containing two phosphorothioated bonds at each end were considerably more toxic to hiPSC and produced lower targeting efficiencies (data not shown).

Even in the absence of Bcl-2, the plasmid V617F donor vector was far superior to ssODN donors for introducing specific point mutations, which may be due to several factors: Transfecting ssODN appeared to be more toxic to hiPSC, even with the interferon-neutralizing B18R protein, which also explains the lower NHEJ rates in these samples. We have previously demonstrated ~2 kb as the optimal homology arm length for hiPSC gene targeting (Byrne et al., 2015); the V617F plasmid donor contained 1.9 kb and 1.3 kb flanking homology arms—far longer than the 110 bp ssODN. We have also reported that circular plasmids have higher nucleofection efficiencies than linear plasmids (Byrne et al., 2015). Circular plasmids may persist longer inside the cells than an ssODN—indeed, culturing the cells for 17 days after transfection was necessary to completely eliminate unincorporated plasmid. Finally, oligo-mediated gene targeting may involve a single-strand annealing mechanism rather than traditional HR. While other groups have demonstrated equal or higher gene targeting with ssODN compared to plasmid or dsODN donors (Chen et al., 2011; Richardson et al., 2016; Soldner et al., 2011), we achieved optimal results using a plasmid donor containing longer homology arms for Cas9 nucleases in hiPSC.

Many methods have been developed to improve all aspects of Cas9-mediated gene targeting, some of which we have tested in hiPSC. Truncated sgRNAs, which possess 17-19 bp of target complementarity instead of 20 bp, have been reported to reduce off-target Cas9 nuclease activity while preserving on-target activity (Fu et al., 2014). However, these studies were done in human tumor cell lines with near-complete gene disruption efficiencies. We developed truncated sgRNAs against hiPSC surface proteins and assayed gene disruption efficiencies by flow cytometry. This more stringent assay revealed that truncated sgRNAs showed reduced on-target activity, yet no consistent decrease in nuclease toxicity, when compared to full length sgRNA controls (FIG. 12). However, the endonuclease Trex2 (Certo et al., 2012) increased gene disruption frequencies by making NHEJ more error-prone in hiPSC (FIG. 12). The blunt-ended dsDNA breaks made by Cas9 are often re-ligated perfectly by canonical NHEJ, so indel frequency is an imperfect measure of the total cutting frequency (Bétermier et al., 2014).

Figure 9D:
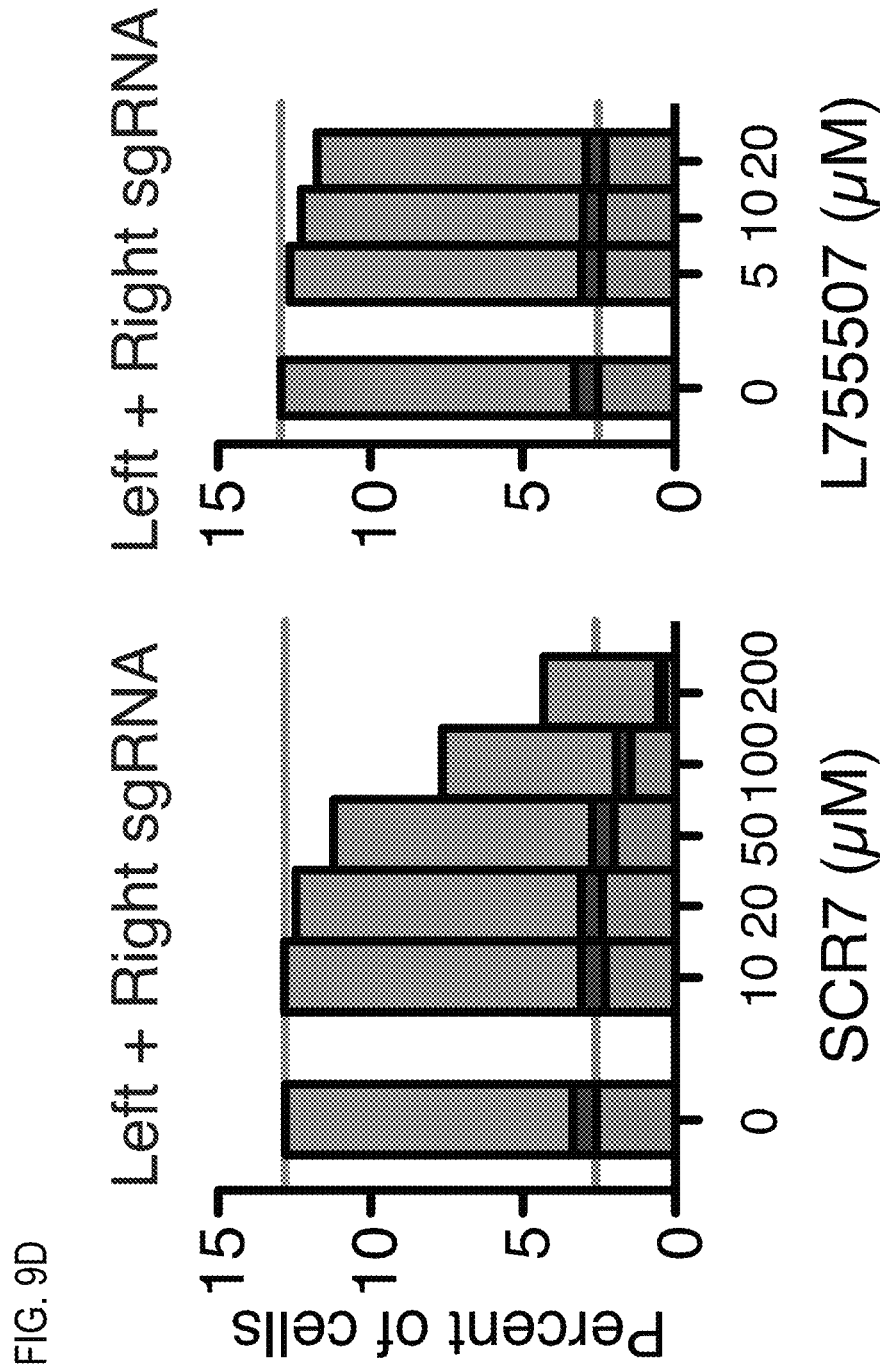
Figure 9E:
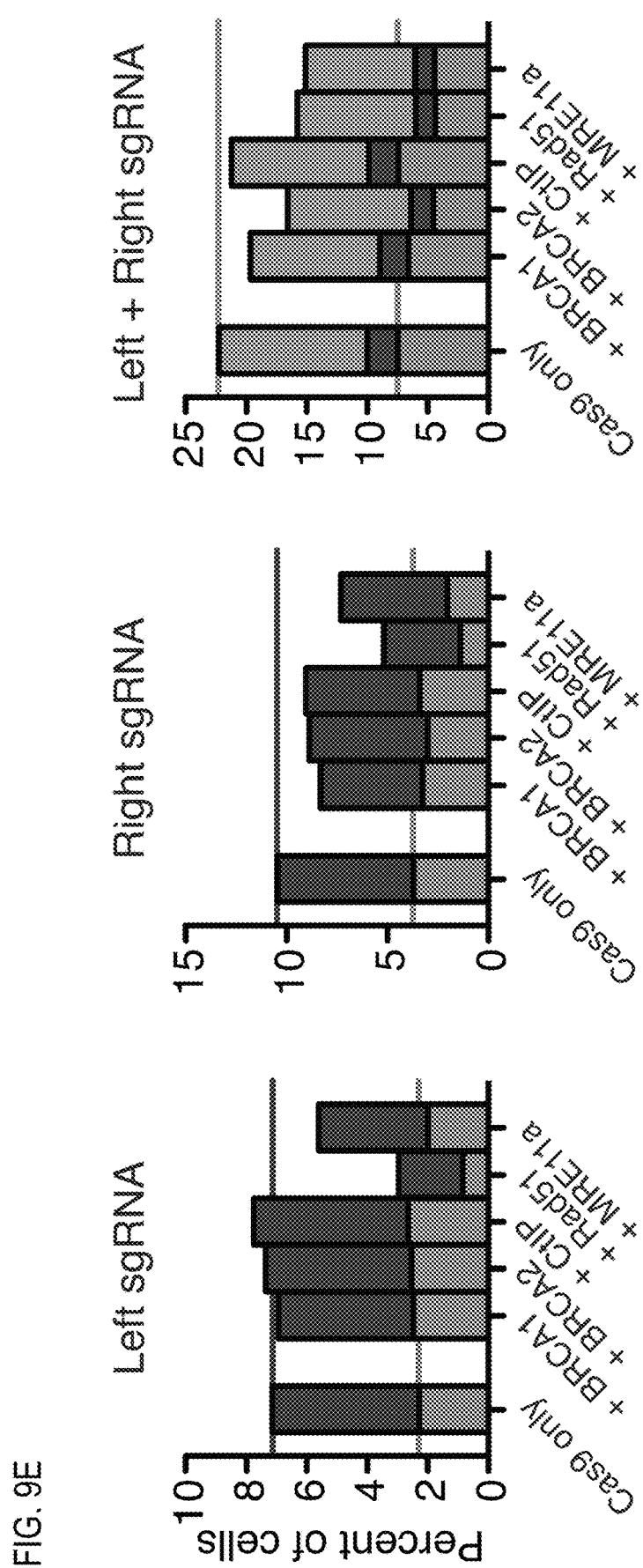
Figure 9F:
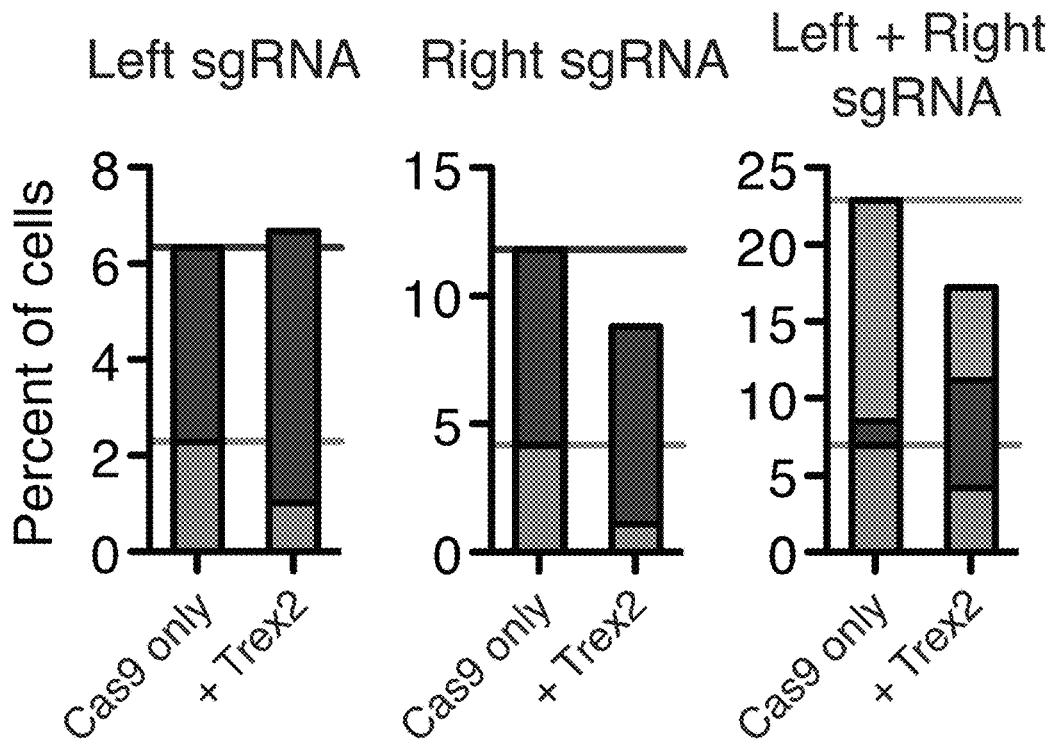
Figure 9G:
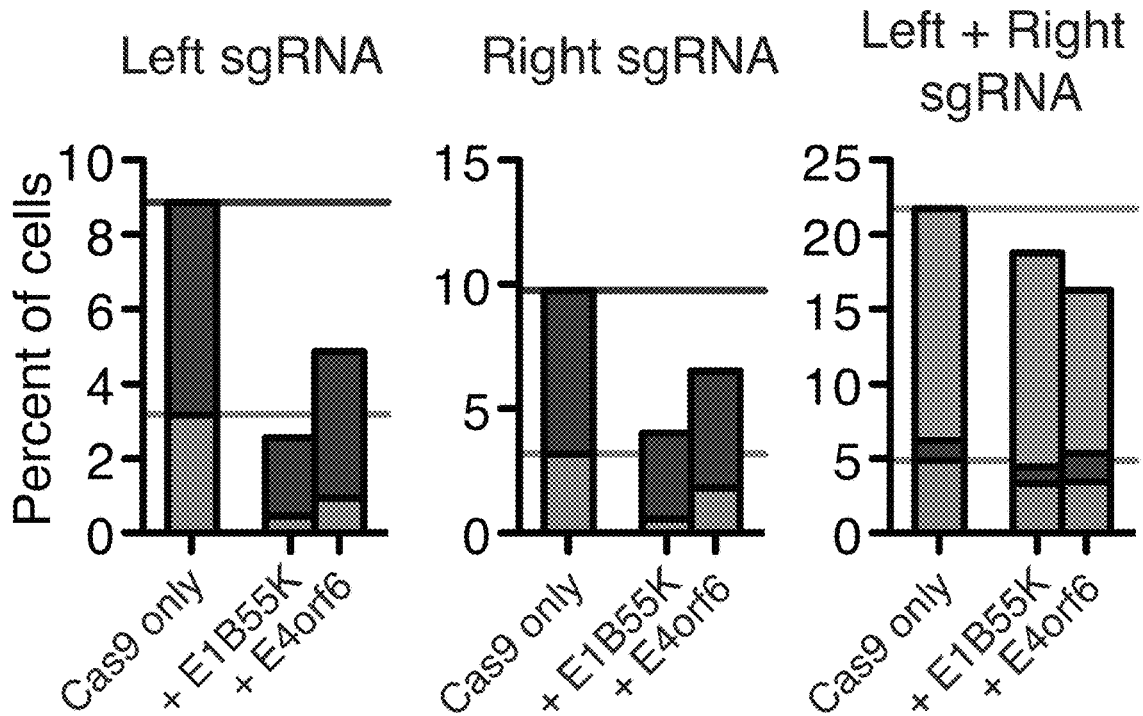

Other methods sought to improve gene targeting by inhibiting NHEJ or enhancing HR, which we also tested with our mThy1 gene targeting system in hiPSC. Unfortunately, neither the DNA ligase IV inhibitor SCR7 (Maruyama et al., 2015) nor the β3-adrenergic receptor agonist L755507 (Yu et al., 2015) improved mThy1 gene targeting efficiencies in PGP1 hiPSC when administered after plasmid nucleofection (FIG. 9D). Brefeldin A, which blocks protein transport to the Golgi, was toxic to PGP1 hiPSC at 0.1 μM (data not shown). Adding plasmids to overexpress principal HR mediators BRCA1, BRCA2, CtIP, and MRE11a into the hiPSC transfection did not improve mThy1 gene targeting efficiency; paradoxically, overexpressing Rad51 reduced gene targeting efficiency (FIG. 9E). Adding Trex2 also reduced mThy1 gene targeting efficiency, likely due to an increased frequency of indel mutations competing with the gene replacement (FIG. 9F). Overexpressing the adenoviral DNA ligase IV inhibitor genes E1B55K or E4orf6 (Chu et al., 2015) reduced mThy1 gene targeting efficiency (FIG. 9G). Human iPSC possessing mutations in DNA ligase IV show impaired NHEJ, but also accumulate dsDNA breaks with increased apoptosis (Tilgner et al., 2013). Many differences between the experimental systems used, including cell line and kinetics, may explain why our results differ from those previously published; however, robust techniques to improve gene targeting remain a topic of intense interest. Therefore, by simply adding Bcl-2 onto the Cas9 nuclease plasmid, we are able to ameliorate nuclease-mediated death and increase the absolute frequency of successful gene editing in hiPSC using a single transfection without enrichment or selection.

REFERENCES

Adams et al. (2010). ATM-independent, high-fidelity non-homologous end joining predominates in human embryonic stem cells. Aging (Albany N.Y.) 2, 582-596.

Ardehali et al. (2011). Overexpression of BCL2 enhances survival of human embryonic stem cells during stress and obviates the requirement for serum factors. Proc. Natl. Acad. Sci. U.S.A. 108, 3282-3287.

Bai et al. (2012). Bcl-$x_L$ enhances single-cell survival and expansion of human embryonic stem cells without affecting self-renewal. Stem Cell Research 8, 26-37.

Ball et al. (2012). A public resource facilitating clinical use of genomes. Proc. Natl. Acad. Sci. U.S.A. 109, 11920-11927.

Berger et al. (2006). Identification of Early Intermediates of Caspase Activation Using Selective Inhibitors and Activity-Based Probes. Molecular Cell 23, 509-521.

Bétermier et al. (2014). Is non-homologous end-joining really an inherently error-prone process? PLoS Genet. 10, e1004086.

Byrne et al. (2015). Multi-kilobase homozygous targeted gene replacement in human induced pluripotent stem cells. Nucleic Acids Research 43, e21.

Certo et al. (2012). Coupling endonucleases with DNA end-processing enzymes to drive gene disruption. Nature Methods 9, 973-975.

Cervantes et al. (2002). Embryonic stem cells and somatic cells differ in mutation frequency and type. Proc. Natl. Acad. Sci. U.S.A. 99, 3586-3590.

Chari et al. (2015). Unraveling CRISPR-Cas9 genome engineering parameters via a library-on-library approach. Nature Methods 12, 823-826.

Chavez et al. (2015). Highly efficient Cas9-mediated transcriptional programming. Nature Methods 12, 326-328.

Chen et al. (2010). Distinct Clinical Phenotypes Associated with JAK2V617F Reflect Differential STAT1 Signaling. Cancer Cell 18, 524-535.

Chen et al. (2011). High-frequency genome editing using ssDNA oligonucleotides with zinc-finger nucleases. Nature Methods 8, 753-755.

Cheng et al. (1997). Conversion of Bcl-2 to a Bax-like death effector by caspases. Science 278, 1966-1968.

Cheng et al. (2001). BCL-2, BCL-X(L) sequester BH3 domain-only molecules preventing BAX- and BAK-mediated mitochondrial apoptosis. Molecular Cell 8, 705-711.

Chu et al. (2015). Increasing the efficiency of homology-directed repair for CRISPR-Cas9-induced precise gene editing in mammalian cells. Nature Biotechnology 33, 543-548.

Cortez et al. (1999). Requirement of ATM-dependent phosphorylation of brca1 in the DNA damage response to double-strand breaks. Science 286, 1162-1166.

Dumitru et al. (2012). Human Embryonic Stem Cells Have Constitutively Active Bax at the Golgi and Are Primed to Undergo Rapid Apoptosis. Molecular Cell 46, 573-583.

Fu et al. (2014). Improving CRISPR-Cas nuclease specificity using truncated guide RNAs. Nature Biotechnology 32, 279-284.

Gafni et al. (2013). Derivation of novel human ground state naive pluripotent stem cells. Nature 504, 282-286.

Garcia-Calvo et al. (1998). Inhibition of human caspases by peptide-based and macromolecular inhibitors. J. Biol. Chem. 273, 32608-32613.

Garcia et al. (2014). Topoisomerase I inhibitor, camptothecin, induces apoptogenic signaling in human embryonic stem cells. Stem Cell Research 12, 400-414.

Garitaonandia et al. (2015). Increased Risk of Genetic and Epigenetic Instability in Human Embryonic Stem Cells Associated with Specific Culture Conditions. PLoS ONE 10, e0118307.

Golding et al. (2007). Extracellular Signal-Related Kinase Positively Regulates Ataxia Telangiectasia Mutated, Homologous Recombination Repair, and the DNA Damage Response. Cancer Research 67, 1046-1053.

Grandela et al. (2007). p53 is required for etoposide-induced apoptosis of human embryonic stem cells. Stem Cell Research 1, 116-128.

Guell et al. (2014). Genome editing assessment using CRISPR Genome Analyzer (CRISPR-GA). Bioinformatics 30, 2968-2970.

Hahn et al. (2002). Enumeration of the Simian Virus 40 Early Region Elements Necessary for Human Cell Transformation. Mol. Cell. Biol. 22, 2111-2123.

Huang et al. (1997). The anti-apoptosis function of Bcl-2 can be genetically separated from its inhibitory effect on cell cycle entry. Embo J. 16, 4628-4638.

International Stem Cell Initiative et al. (2011). Screening ethnically diverse human embryonic stem cells identifies a chromosome 20 minimal amplicon conferring growth advantage. Nature Biotechnology 29, 1132-1144.

Janumyan et al. (2003). Bcl-$x_L$/Bcl-2 coordinately regulates apoptosis, cell cycle arrest and cell cycle entry. Embo J. 22, 5459-5470.

Kawamura et al. (2009). Linking the p53 tumour suppressor pathway to somatic cell reprogramming. Nature 460, 1140-1144.

Laulier et al. (2012). The secret life of Bcl-2: apoptosis-independent inhibition of DNA repair by Bcl-2 family members. Mutat. Res. 751, 247-257.

Lee et al. (2013). Tumorigenicity as a clinical hurdle for pluripotent stem cell therapies. Nature Medicine 19, 998-1004.

Lee et al. (2009). A Robust Approach to Identifying Tissue-Specific Gene Expression Regulatory Variants Using Personalized Human Induced Pluripotent Stem Cells. PLoS Genet. 5, e1000718.

Liu et al. (2013). High Mitochondrial Priming Sensitizes hESCs to DNA-Damage-Induced Apoptosis. Cell Stem Cell 13, 483-491.

Liu et al. (2014). Stem cells: balancing resistance and sensitivity to DNA damage. Trends in Cell Biology 24, 268-274.

Mali et al. (2013). RNA-guided human genome engineering via Cas9. Science 339, 823-826.

Maruyama et al. (2015). Increasing the efficiency of precise genome editing with CRISPR-Cas9 by inhibition of non-homologous end joining. Nature Biotechnology 33, 538-542.

Maurer et al. (2006). Glycogen synthase kinase-3 regulates mitochondrial outer membrane permeabilization and apoptosis by destabilization of MCL-1. Molecular Cell 21, 749-760.

Mayshar et al. (2010). Identification and classification of chromosomal aberrations in human induced pluripotent stem cells. Cell Stem Cell 7, 521-531.

McStay & Green (2014). Measuring apoptosis: caspase inhibitors and activity assays. Cold Spring Harb Protoc 2014, 799-806.

Moldoveanu et al. (2014). Many players in BCL-2 family affairs. Trends in Biochemical Sciences 39, 101-111.

Momcilovic et al. (2010). DNA Damage Responses in Human Induced Pluripotent Stem Cells and Embryonic Stem Cells. PLoS ONE 5, e13410.

Monaco et al. (2013). The selective BH4-domain biology of Bcl-2-family members: IP3Rs and beyond. Cell. Mol. Life Sci. 70, 1171-1183.

Nagaria et al. (2013). DNA double-strand break response in stem cells: mechanisms to maintain genomic integrity. Biochim. Biophys. Acta 1830, 2345-2353.

ORFeome Collaboration (2016). The ORFeome Collaboration: a genome-scale human ORF-clone resource. Nature Methods 13, 191-192.

Peixoto et al. (2009). MAC inhibitors suppress mitochondrial apoptosis. Biochem. J. 423, 381-387.

Pratt et al. (2012). The latent membrane protein 1 (LMP1) oncogene of Epstein-Barr virus can simultaneously induce and inhibit apoptosis in B cells. J. Virol. 86, 4380-4393.

Qin et al. (2007). Regulation of Apoptosis and Differentiation by p53 in Human Embryonic Stem Cells. Journal of Biological Chemistry 282, 5842-5852.

Richardson et al. (2016) Enhancing homology-directed genome editing by catalytically active and inactive CRISPR-Cas9 using asymmetric donor DNA. Nature Biotechnology.

Slaymaker et al., Rationally engineered Cas9 nucleases with improved specificity, 2016 Jan. 1; 351(6268):84-88.

Shalem et al. (2014). Genome-Scale CRISPR-Cas9 Knock-out Screening in Human Cells. Science 343, 84-87.

Smith et al. (2014). Efficient and Allele-Specific Genome Editing of Disease Loci in Human iPSCs. Molecular Therapy 23, 570-577.

Soldner et al. (2011). Generation of Isogenic Pluripotent Stem Cells Differing Exclusively at Two Early Onset Parkinson Point Mutations. Cell 146, 318-331.

Tilgner et al. (2013). A human iPSC model of Ligase IV deficiency reveals an important role for NHEJ-mediated-DSB repair in the survival and genomic stability of induced pluripotent stem cells and emerging haematopoietic progenitors. Cell Death Differ 20, 1089-1100.

Wang et al. (2001). Transient Expression of Wild-type or Mitochondrially Targeted Bcl-2 Induces Apoptosis, whereas Transient Expression of Endoplasmic Reticulum-targeted Bcl-2 Is Protective against Bax-induced Cell Death. Journal of Biological Chemistry 276, 44117-44128.

Wang et al. (2009). Inhibition of Caspase-mediated Anoikis Is Critical for Basic Fibroblast Growth Factor-sustained Culture of Human Pluripotent Stem Cells. Journal of Biological Chemistry 284, 34054-34064.

Wang et al. (2002). Inhibition of cancer cell growth by BRCA2. Cancer Research 62, 1311-1314.

Yoshida et al. (2004). Bax-inhibiting peptide derived from mouse and rat Ku70. Biochemical and Biophysical Research Communications 321, 961-966.

Youle et al. (2008). The BCL-2 protein family: opposing activities that mediate cell death. Nature Reviews Molecular Cell Biology 9, 47-59.

Youn et al. (2004). Bcl-2 expression suppresses mismatch repair activity through inhibition of E2F transcriptional activity. Nature Cell Biology 7, 137-147.

Yu et al. (2015). Small molecules enhance CRISPR genome editing in pluripotent stem cells. Cell Stem Cell 16, 142-147.

Zhao et al. (2008). Two supporting factors greatly improve the efficiency of human iPSC generation. Cell Stem Cell 3, 475-479.

Arnould et al., "The I-CreI meganuclease and its engineered derivatives: applications from cell modification to gene therapy," Prot. Eng. Des. Sel. 2011, 24:27-31.

Cong et al., "Multiplex genome engineering using CRISPR/Cas systems," Science, 2013, 339(6121): p. 819-23.

Drawnel et al., "Disease modeling and phenotypic drug screening for diabetic cardiomyopathy using human induced pluripotent stem cells," Cell Rep. 2014; 9, 810-21.

Friedland et al., "Heritable genome editing in C. elegans via a CRISPR-Cas9 system," Nat Methods, 2013. 10(8): pp. 741-43.

Hwang et al., "Efficient genome editing in zebrafish using a CRISPR-Cas system," Nat Biotechnol, 2013, 31:227-29.

Jiang et al., "RNA-guided editing of bacterial genomes using CRISPR-Cas systems," Nat Biotechnol, 2013, 31:233-39.

Jinek et al., "A programmable dual-RNA-guided DNA endonuclease in adaptive bacterial immunity," Science, 2012. 337(6096): p. 816-21.

Jinek et al., "RNA-programmed genome editing in human cells," elife, 2013. 2: p. e00471.

Kleinstiver et al., "High-fidelity CRISPR-Cas9 nucleases with no detectable genome-wide off-target effects," Nature 2016 529:490-95.

Li et al., "Precise correction of the dystrophin gene in duchenne muscular dystrophy patient induced pluripotent stem cells by TALEN and CrISPR-Cas9," Stem Cell Reports 4, 143-54, 2015.

Mali et al., "CAS9 transcriptional activators for target specificity screening and paired nickases for cooperative genome engineering," Nature Biotechnology 31, 833-838 (2013).

Makarova et al., Nature Reviews, Microbiology, Vol. 9, June 2011, pp. 467-477.

Pant & Lozano, "Limiting the power of p53 through the ubiquitin proteasome pathway," Genes Dev. 28, 1739-51, 2014.

Robinton & Daley, "The promise of induced pluripotent stem cells in research and therapy," Nature 481, 295-305, 2012.

Shui et al., "The Rise of CRISPR/Cas for Genome Editing in Stem Cells," Stem Cells International Volume 2016, Article ID 8140168, 17 pages.

Takahashi et al., "Induction of pluripotent stem cells from adult human fibroblasts by defined factors," Cell 131, 861-72, 2007.

Thermes et al., "I-SceI meganuclease mediates highly efficient transgenesis in fish," Mech. Dev. 2002 October; 118(1-2):91-98.

Tsvetkov et al., "Ubiquitin-independent p53 proteasomal degradation," Cell Death Differ. 17, 103-08, 2010.

Yin et al., "Genome editing with Cas9 in adult mice corrects a disease mutation and phenotype," Nat Biotechnol, 2014. 32(6): p. 551-53.

Yu et al., "Induced pluripotent stem cell lines derived from human somatic cells," Science 318, 1917-20, 2007.

The invention claimed is:

1. A method of improving efficiency of targeting in a stem cell, comprising
    expressing Cas9 and Bcl-2 in a genetically modified stem cell comprising an expression construct encoding the Cas9 and Bcl-2,
and
    providing the stem cell with a first single guide RNA (sgRNA) complementary to a first target nucleic acid sequence of the stem cell genome,
    wherein efficiency of targeting of the Cas9 to the first target nucleic acid sequence is increased relative to Cas9 targeting without overexpression of Bcl-2.

2. The method of claim 1, further comprising contacting the stem cell with a caspase inhibitor.

3. The method of claim 1, further comprising contacting the stem cell with a p38 MAP kinase inhibitor.

4. The method of claim 1, wherein the stem cell is an embryonic stem cell (ESC).

5. The method of claim 1, wherein the stem cell is a somatic stem cell.

6. The method of claim 5, wherein the somatic stem cell is selected from the group consisting of an inducible pluripotent stem cell, a hematopoietic stem cell, a neural stem cell, and a mesenchymal stem cell.

7. The method of claim 1, wherein the stem cell is a human stem cell.

8. The method of claim 1 wherein the stem cell includes an expression construct encoding the first single guide RNA (sgRNA).

9. The method of claim 1 wherein the stem cell includes an expression construct encoding a plurality of sgRNAs complementary to a plurality of target nucleic acid sequences.

10. The method of claim 1 wherein the stem cell includes an expression construct encoding an anti-apoptosis protein selected from the group consisting of a dominant negative mutant of p53 (DN p53), a mouse double minute 2 homolog (MDM2), a p53-induced protein with a RING (Really Interesting New Gene)-H2 domain (Pirh2, RCHY1), a constitutively photo-morphogenic 1 (COP1), an ARF (Alternative Reading Frame) Binding Protein 1 (ARF-BP1, HUWE1), Bcl2A1, Bcl-$x_L$, Mcl-1, Bcl-w, and Bcl-B.

11. The method of claim 1 further comprising providing to the stem cell an RNA inhibitor of p53, an oligonucleotide inhibitor of p53, or a Bax channel inhibitor.

12. The method of claim 1 wherein the Cas9 is a Cas9 nuclease, a Cas9 nickase or a nuclease-null Cas9 fused to a nuclease domain.

* * * * *